United States Patent
Kello et al.

(10) Patent No.: US 11,983,749 B2
(45) Date of Patent: May 14, 2024

(54) SYSTEM AND METHOD FOR AUTOMATING ELECTRONIC PHARMACEUTICAL TRANSACTIONS

(71) Applicant: Breckenridge Capital LLC, Royal Oak, MI (US)

(72) Inventors: John Kello, Bloomfield Hills, MI (US); Gablan Zawaideh, Bloomfield Hills, MI (US)

(73) Assignee: BRECKENRIDGE CAPITAL LLC, Royal Oak, MI (US)

( * ) Notice: Subject to any disclaimer, the term of this patent is extended or adjusted under 35 U.S.C. 154(b) by 509 days.

(21) Appl. No.: 17/104,384

(22) Filed: Nov. 25, 2020

(65) Prior Publication Data
US 2021/0158413 A1 May 27, 2021

Related U.S. Application Data

(60) Provisional application No. 63/113,382, filed on Nov. 13, 2020, provisional application No. 62/939,802, filed on Nov. 25, 2019.

(51) Int. Cl.
*G06Q 30/00* (2023.01)
*A61J 1/03* (2023.01)
(Continued)

(52) U.S. Cl.
CPC .......... *G06Q 30/0607* (2013.01); *A61J 1/035* (2013.01); *A61J 1/06* (2013.01);
(Continued)

(58) Field of Classification Search
None
See application file for complete search history.

(56) References Cited

U.S. PATENT DOCUMENTS

| | | | | |
|---|---|---|---|---|
| 5,072,383 A | * | 12/1991 | Brimm | G16H 70/60 705/2 |
| 5,597,995 A | * | 1/1997 | Williams | G06V 20/66 235/375 |

(Continued)

FOREIGN PATENT DOCUMENTS

| | | | | |
|---|---|---|---|---|
| CA | 2787100 A1 | * | 9/2011 | G06F 16/955 |
| CA | 2842430 A1 | * | 6/2013 | G06Q 30/018 |

(Continued)

OTHER PUBLICATIONS

Match RX; https://web.archive.org/web/20170929042009/https://www.matchrx.com/ (Year: 2017).*

(Continued)

*Primary Examiner* — James A Reagan
(74) *Attorney, Agent, or Firm* — The Dobrusin Law Firm, P.C.; Daniela M. Thompson-Walters

(57) ABSTRACT

An electronic transaction system for selling and purchasing regulated products having: a) one or more servers; b) an application which is a computer program; wherein the application includes: i) one or more validation heuristics; and ii) one or more member incentive heuristics; and c) one or more databases which store: i) the plurality of jurisdiction-based rules; ii) a plurality of regulated products; iii) one or more member incentives; and iv) a plurality of merchant accounts associated with the plurality of merchants.

20 Claims, 9 Drawing Sheets

(51) Int. Cl.
| | |
|---|---|
| *A61J 1/06* | (2006.01) |
| *G06Q 10/0832* | (2023.01) |
| *G06Q 20/08* | (2012.01) |
| *G06Q 20/38* | (2012.01) |
| *G06Q 20/40* | (2012.01) |
| *G06Q 30/018* | (2023.01) |
| *G06Q 30/0207* | (2023.01) |
| *G06Q 30/0282* | (2023.01) |
| *G06Q 30/0601* | (2023.01) |
| *G06Q 50/26* | (2012.01) |
| *G16H 40/20* | (2018.01) |

(52) U.S. Cl.
CPC ....... *G06Q 10/0832* (2013.01); *G06Q 20/085* (2013.01); *G06Q 20/383* (2013.01); *G06Q 20/405* (2013.01); *G06Q 30/0185* (2013.01); *G06Q 30/0236* (2013.01); *G06Q 30/0282* (2013.01); *G06Q 30/0609* (2013.01); *G06Q 30/0633* (2013.01); *G06Q 50/26* (2013.01); *G16H 40/20* (2018.01)

(56) References Cited

U.S. PATENT DOCUMENTS

| | | | | |
|---|---|---|---|---|
| 5,619,991 A * | 4/1997 | Sloane | A61B 5/0002 | 600/300 |
| 5,737,539 A * | 4/1998 | Edelson | G16H 10/60 | 705/2 |
| 5,758,095 A * | 5/1998 | Albaum | G06Q 30/0601 | 715/236 |
| 5,845,255 A * | 12/1998 | Mayaud | G16Z 99/00 | 705/3 |
| 5,907,493 A * | 5/1999 | Boyer | G07F 9/002 | 700/231 |
| 5,911,687 A * | 6/1999 | Sato | G16H 40/20 | 600/300 |
| 5,970,462 A * | 10/1999 | Reichert | G16H 80/00 | 705/2 |
| 6,064,968 A * | 5/2000 | Schanz | G06Q 10/10 | 706/924 |
| 6,202,923 B1 * | 3/2001 | Boyer | G06V 20/66 | 235/383 |
| 6,539,281 B2 * | 3/2003 | Wan | G07F 17/0092 | 700/244 |
| 6,606,744 B1 * | 8/2003 | Mikurak | H04L 9/40 | 717/174 |
| 6,711,460 B1 * | 3/2004 | Reese | G16H 20/10 | 700/216 |
| 7,058,584 B2 * | 6/2006 | Kosinski | G16H 20/10 | 379/93.12 |
| 7,111,780 B2 * | 9/2006 | Broussard | G16H 20/13 | 235/380 |
| 7,734,478 B2 * | 6/2010 | Goodall | G16H 20/10 | 705/2 |
| 7,775,056 B2 * | 8/2010 | Lowenstein | G06Q 10/087 | 705/28 |
| 7,885,856 B1 * | 2/2011 | Berger | G06Q 30/0633 | 705/26.41 |
| 8,271,336 B2 * | 9/2012 | Mikurak | G06Q 50/12 | 705/7.29 |
| 8,983,869 B2 * | 3/2015 | Flanagan | G06Q 30/0607 | 705/317 |
| 10,235,499 B1 * | 3/2019 | Bleser | G06Q 10/087 | |
| 10,373,713 B1 * | 8/2019 | Kello | G16H 40/20 | |
| 10,395,185 B2 * | 8/2019 | Dick | G06Q 10/00 | |
| 10,482,396 B2 * | 11/2019 | Dick | G06Q 10/00 | |
| 10,769,689 B2 * | 9/2020 | Flanagan | G06Q 30/018 | |
| 11,587,135 B2 * | 2/2023 | Flanagan | G06Q 30/018 | |
| 2002/0153411 A1 * | 10/2002 | Wan | G16H 20/10 | 235/375 |
| 2003/0149599 A1 * | 8/2003 | Goodall | G16H 20/10 | 705/2 |
| 2003/0179287 A1 * | 9/2003 | Kozic | H04N 7/147 | 348/14.08 |
| 2003/0225595 A1 * | 12/2003 | Helmus | G06Q 40/08 | 705/2 |
| 2004/0064351 A1 * | 4/2004 | Mikurak | G06Q 30/0269 | 705/22 |
| 2004/0073498 A1 * | 4/2004 | Breen, Jr. | G06Q 30/0621 | 705/26.5 |
| 2004/0230503 A1 * | 11/2004 | Lucas | G06Q 10/06 | 705/28 |
| 2005/0177392 A1 * | 8/2005 | Domashnev | G06Q 30/06 | 705/2 |
| 2007/0100653 A1 * | 5/2007 | Ramer | G06Q 30/06 | 705/347 |
| 2008/0269947 A1 * | 10/2008 | Beane | G06Q 20/12 | 700/241 |
| 2009/0043672 A1 * | 2/2009 | Ourega | G06Q 30/0633 | 705/26.8 |
| 2009/0083064 A1 * | 3/2009 | Mahinda | G06Q 30/00 | 705/2 |
| 2010/0121752 A1 * | 5/2010 | Banigan | G06Q 40/04 | 705/37 |
| 2012/0190386 A1 * | 7/2012 | Anderson | G01S 19/14 | 455/456.3 |
| 2013/0151373 A1 * | 6/2013 | Flanagan | G06Q 30/018 | 705/26.25 |
| 2014/0288959 A1 * | 9/2014 | Schoenberg | G06Q 10/06 | 705/2 |
| 2014/0316797 A1 * | 10/2014 | Biernacki | G16H 50/30 | 705/2 |
| 2015/0154673 A1 * | 6/2015 | Flanagan | G06Q 30/0607 | 705/26.25 |
| 2019/0341139 A1 * | 11/2019 | Kello | G16H 40/00 | |
| 2020/0394692 A1 * | 12/2020 | Flanagan | G06Q 30/018 | |
| 2023/0169556 A1 * | 6/2023 | Flanagan | G06Q 30/0607 | 705/26.25 |

FOREIGN PATENT DOCUMENTS

| | | | | |
|---|---|---|---|---|
| CN | 104364816 A * | 2/2015 | ........ | G06Q 30/018 |
| JP | 2000331110 A * | 11/2000 | ........ | G06F 17/60 |
| JP | 2002230651 A * | 8/2002 | ........ | G06F 17/60 |
| JP | 2007026035 A | 2/2007 | | |
| JP | 2016006600 A * | 1/2016 | ........ | G06F 19/00 |
| JP | 2019175484 A * | 10/2019 | ........ | A61J 1/03 |
| JP | 2019215658 A * | 12/2019 | ........ | G06Q 10/06 |
| WO | WO-2013086335 A1 * | 6/2013 | ........ | G06Q 30/018 |
| WO | WO-2013138723 A1 * | 9/2013 | ........ | G06Q 10/06 |

OTHER PUBLICATIONS

Fiona Masterson. "Factors that Facilitate Regulatory Approval for Drug/Device Combination Products in the European Union and United States of America: A Mixed Method Study of Industry Views." (Sep. 2015). Retrieved online Aug. 29, 2023. (Year: 2015) https://aran.library.nuigalway.ie/bitstream/handle/10379/5542/Doctorate%20Fiona%20Masterson.pdf?sequence=1 (Year: 2015).*

* cited by examiner

| Reward Type | Transaction Criteria (completed orders) | Context | Platinum | Gold | Silver | Bronze |
|---|---|---|---|---|---|---|
| | | | Average 20+ or more transactions (buy/sell) per month | Average 9 to < 20 transactions (buy/sell) per month | Average 3 to < 9 transactions (buy/sell) per month | Average < 3 transactions (buy/sell) per month |
| Buyer | Buy Escrow | Adding to cart and Order checkout | $40,000 | $30,000 | $25,000 | $20,000 |
| Buyer | Free ground shipping on purchases of $500+ | Order Checkout | First Friday of the month | First Friday of the month | First Friday of the month | Not applicable |
| Seller | 40+ or more open postings (unique posting IDs) at time of sale | Order Checkout / Seller Confirmation | 7.5% seller fee | 7.5% seller fee | Not applicable | Not applicable |
| Seller | 50+ or more open postings (unique posting IDs) at time of sale | Order Checkout / Seller confirmation | 7.5% seller fee | 7.5% seller fee | 7.5% seller fee | 7.5% seller fee |
| Buyer | Buying order minimum (money) | Order Checkout | $15 | $15 | $15 | $15 |
| Seller | Selling fee if number of items posted (unique posting IDs) in the lifetime is between 0 to 24 | Order Checkout / Seller confirmation | 12% Seller Fee | 12% Seller Fee | 12% Seller Fee | 12% Seller Fee |
| Seller | Selling fee if number of items posted (unique posting IDs) in the lifetime is more than or equal to 25 | Order Checkout / Seller COnfirmation | 9.5% Seller Fee | 9.5% Seller Fee | 9.5% Seller Fee | 9.5% Seller Fee |
| Buyer | Early Wishlist (2+ hours earlier) | Wishlist | Yes | Not applicable | Not applicable | Not applicable |
| Seller | Wave $2.50 Seller Pickup Fee | Order Checkout / Seller COnfirmation | Yes | Not applicable | Not applicable | Not applicable |

SYSTEM AND METHOD FOR AUTOMATING ELECTRONIC PHARMACEUTICAL TRANSACTIONS

CROSS REFERENCE TO RELATED APPLICATIONS

Applicant claims the benefit of both U.S. Provisional Application No. 62/939,802 filed on Nov. 25, 2019 and U.S. Provisional Application No. 63/113,382 filed on Nov. 13, 2020, the contents of which are incorporated herein by reference in their entirety.

FIELD

The present teachings relate to a transaction system and method for automating the electronic transaction of goods, more particularly, regulated products such as pharmaceutical products. The system and method may be advantageous for use between pharmacies and allowing for the sale, resale, and distribution of pharmaceutical products. The system and method may be particularly advantageous for automatically ensuring sales between pharmacies are compliant with regulations relating to the sale of pharmaceutical products while also promoting and encouraging continued use of an online system.

BACKGROUND

Pharmaceutical products are regulated substances which are only able to be sold and distributed through properly licensed entities such as wholesalers and pharmacies. Regulations are applied at both the federal and state levels. Different states may have different licensing requirements and different laws pertaining to the resale of prescription medications that occur between licensed pharmacies, sale of prescription medications that occur between licensed pharmacies and wholesalers, or both. Pharmacies operating in one jurisdiction (e.g., state) may not know the regulations applicable to pharmacies operating in other jurisdictions (e.g., other states) and thus are unable to quickly ascertain if a transaction between themselves and an out-of-jurisdiction pharmacy is compliant with the regulations applicable to both entities. During in-person transactions between pharmacies, at some point prior to completing a transaction, the pharmacies must determine each other's identity and associated jurisdiction, thus providing an opportunity to research the applicable regulations imposed on each pharmacy. In an online transaction system, this challenge is further amplified as a technical problem rooted in the technology, in that the pharmacies acting as buyers may not know the identity of the pharmacies acting as sellers, and thus may not know what jurisdiction the sellers are associated with, and vice-versa. It may be beneficial to keep an electronic marketplace and transactions anonymous, so that buyers do not favor some sellers over others, sellers are motivated to fairly price their products, and buyers do not try to contact sellers separately from the transaction system to complete a transaction in-person and outside of the system itself.

Another challenge is the managing of internal stock within a pharmacy and the associated expiration dates of pharmaceutical products. Pharmacies typically purchase new, unopened packages from wholesale distributors but may not have enough customers to use the stock before its expiration. Sellers of nonregulated products typically address this type of challenge by offering discounts and increasing advertising to promote purchase of products before or around their expiration. As pharmaceutical products are prescription-based, a pharmacy must wait for a patient to arrive with a prescription for the pharmaceutical product. And even then, the patient may only need a portion of the pharmaceutical product and not the entire available stock.

In an effort to address these challenges, online systems have been created to allow for the sale, resale, and distribution of full and partial pharmaceutical products between pharmacies. For example, U.S. Pat. No. 10,373,713 teaches an efficient online system and method for the method of selling, reselling, and distributing pharmaceutical products among pharmacies and is incorporated herein by reference in its entirety for all purposes. Notwithstanding the above, there is still a need for an online system that addresses the regulation requirements and allows for redistribution of partial packages (e.g., opened, unsealed) of pharmaceutical products.

Another technical problem encountered by pharmacy to pharmacy sales in an online system is the continuous need for pharmacies to both post and purchase pharmaceutical products via the online system. As the available product stock in the system is dependent on the users actively posting, there is a need to continuously encourage users to add products to the system for purchase by others. If a diverse pharmaceutical product offering is not available for sale, potential buyers become disinterested in using the online system and rely on traditional purchasing and distribution methods. If buyers are not purchasing using the online system, sellers are not incentivized to continue adding additional pharmaceutical products from their pharmacy to the inventory listing.

What is needed is a transaction system and method which can ensure both sellers and buyers of regulated products (e.g., pharmaceutical products) are complying with regulations requirements for their sale, resale, and distribution. What is needed is a transaction system which allows for sellers and buyers to remain anonymous from one another. What is needed is a transaction system and method which allows for regulated product merchants (e.g., pharmacies) to share their surplus inventory before regulated products expire. What is needed is a transaction system and method which encourages continued use of the online system by both sellers and buyers so that the inventory is continuously updated to provide a diverse regulated product offering.

SUMMARY

The present disclosure provides for an electronic transaction system for selling and purchasing regulated products comprising: a) one or more servers comprising one or more processors and one or more memory storage devices; b) an application residing on the one or more servers, wherein the application is a computer program which provides for a sale of one or more regulated products from a first merchant to a second merchant, wherein the application includes: i) one or more validation heuristics which automatically confirm compliance of one or more of a plurality of jurisdiction-based rules prior to a completion of a sale of the one or more regulated products from the second merchant to the first merchant; ii) one or more member incentive heuristics which automatically determine one or more incentives available to one or more merchants; c) one or more databases hosted by the one or more servers and accessible by the application via the one or more processors, wherein the one or more databases store: i) the plurality of jurisdiction-based rules pertaining to the sale and purchase of a plurality of regulated products to and from a plurality of merchants in a plurality of jurisdictions; ii) a plurality of regulated products available for purchase by one or more merchants and which includes the one or more regulated products; iii) one or more member incentives automatically determined by the one or more member incentive heuristics; and iv) a plurality of merchant accounts associated with the plurality of merchants.

The present disclosure provides for a method of selling and purchasing one or more regulated products via the electronic transaction system of the present teachings, wherein the method comprises: a) a user, associated with the first merchant and acting in a capacity of a buyer, opening a marketplace page of the application via a first user interface; b) automatically executing by one or more processors at least one of the one or more validation heuristics to identify a plurality of regulated products available for sale by a plurality of second merchants acting in a capacity of a seller and which comply with the jurisdiction-based rules for both the first merchant and the plurality of second merchants; c) automatically displaying the plurality of regulated products identified by the one or more validation heuristics on the marketplace page; d) the user selecting the one or more regulated products from the marketplace page from the first merchant for purchase; and e) automatically executing automated payment from the first merchant to the second merchant to complete the purchase of the one or more regulated products.

The present disclosure may provide on online system which incorporates a plurality of jurisdiction-based requirements pertaining to the sale, resale, and distribution of pharmaceutical products to and from pharmacies in different jurisdictions. Prior to the completion of a transaction, the system may be able to automatically verify via one or more validation heuristics that the jurisdiction-based requirements are being adhered to and either automatically permit or prevent a portion or all of a transaction to proceed. This provides an unconventional approach by alleviating the need for merchants using the system to know the other merchants, their business location, and the regulations applicable to not only themselves, but the other merchant in a transaction. The system may provide the unconventional approach of allowing for the anonymous interaction of buyers and sellers while allowing for the purchase and sale of products between them. This anonymous interaction is only able to be completed via computer-implemented method via the electronic transaction system, as in-person transactions inherently involve the identity of the parties being known to one another. The system may also include one or more member incentive heuristics algorithms which may incentivize one or more users to continuously post for sale, purchase, or both pharmaceutical products to the system. These one or more member incentive heuristics algorithms provide an unconventional approach to incentivizing users to use the system by combining both subjective and objective observations with the transaction system itself and other merchants using the system.

BRIEF DESCRIPTION OF DRAWINGS

FIG. 9 illustrates a benefits chart summarizing benefits for users of the system.

DETAILED DESCRIPTION

Figure 1:
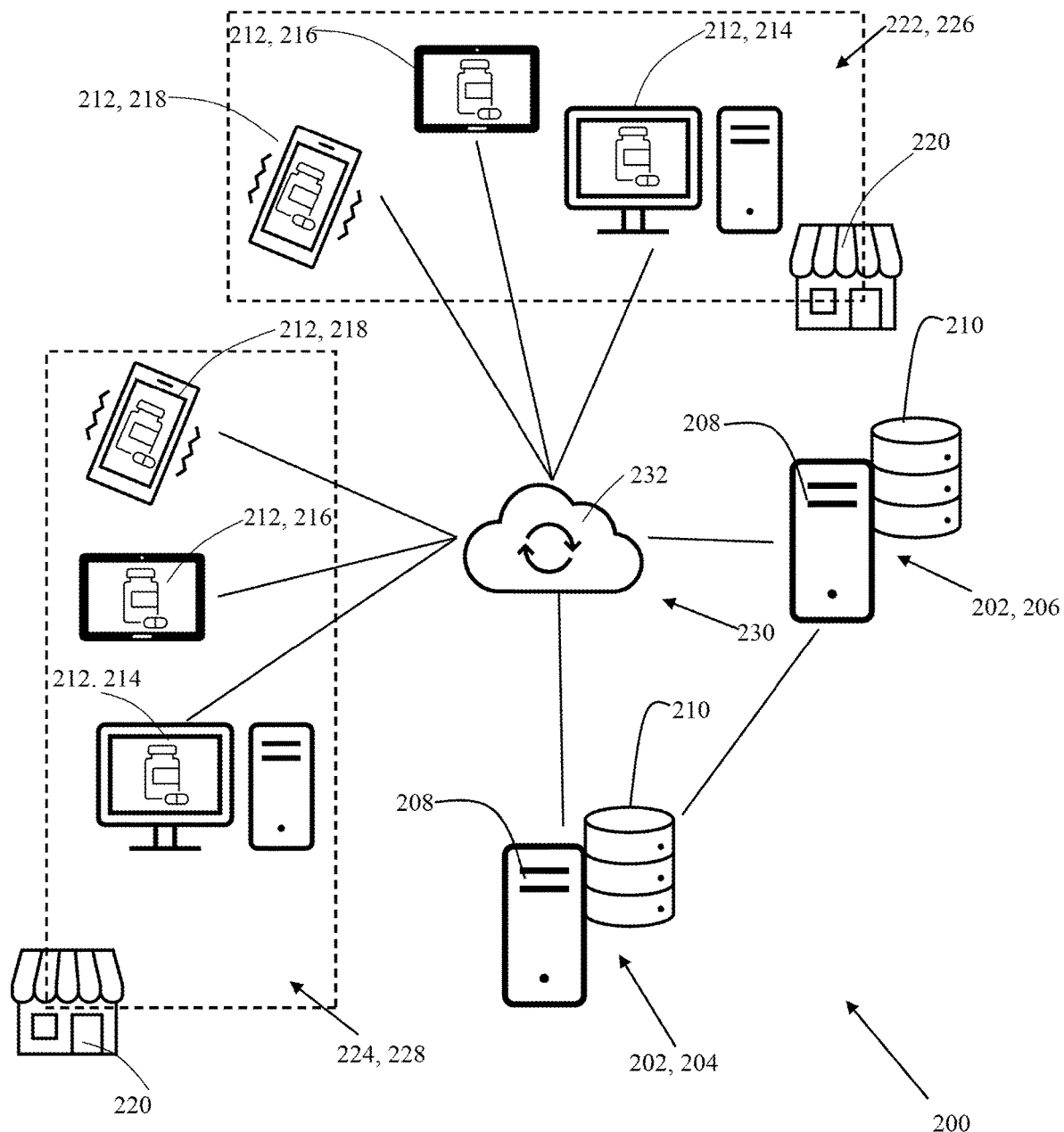
FIG. 1 illustrates a schematic of a transaction system.

The present teachings meet one or more of the above needs by the improved devices and methods described herein. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Regulated Products and Regulated Product Merchants

The present teachings may be particularly advantageous for the sale of regulated products. Regulated products include any products having specific licensing requirements or other regulations for their sale. Regulated products may include pharmaceutical products, cosmetics, food, tobacco, alcohol, firearms, legalized recreational drugs, the like, or any combination thereof. The regulated products, manufacturers, sellers, purchasers, or any combination thereof may require regulatory approvals at federal, state, and/or local levels. Pharmaceutical products may include prescription drugs, biologics, vaccines, the like, or any combination thereof. The regulated products may be provided in packaging from a manufacturer or wholesaler. The original packaging may be considered sealed packaging. The packaging may contain a quantity when originally packaged and distributed. The quantity may be one or a plurality of the regulated product. When the full, original quantity of a pharmaceutical product is within the package, it may be referred to as a sealed and/or a full package. When only a portion of (e.g., less than) the original quantity is within the package, the package is open and no longer sealed, or both it may be referred to as a partial package.

The regulated products may be sold and/or purchased by regulated product merchants. Regulated product merchants may be referred to as merchants. Regulated product merchants may include manufacturers, wholesalers, distributers, retailers, the like, or any combination thereof. Regulated product merchants may be regulated at a local level (e.g., city, county), state level, federal level, or any combination thereof. Merchants for pharmaceutical products may be referred to as pharmacies. Regulated products, including pharmaceutical products, may be purchased and sold by pharmacies. Pharmacies may include retailers authorized in preparing and dispensing of pharmaceutical products to individuals. Pharmacies may generally store an inventory of either or both frequently and infrequently used pharmaceutical products. Pharmacies may be generally regulated at multiple levels, from local to federal level. Regulations may include local regulations, state regulations, federal regulations, the like, or a combination thereof. Regulations may include: a pharmacy license, a National Association of Board of Pharmacy (NABP) number, a National Council for Prescription Drug Programs (NCPDP) number, a Drug Enforcement Agency (DEA) number, an Employer Identification Number (EIN), a National Provider Identifier (NPI) number, the like, or any combination thereof.

Regulated product merchants may interact with one another during a transaction. A transaction may function to allow for one merchant to purchase a regulated product from another merchant. The merchant acting in a buying capacity during a transaction may be referred to as a buyer. The merchant acting in a selling capacity during a transaction may be referred to as a seller. Regulated products offered for sale may be offered for sale and/or resale. As a merchant is typically an entity and not an individual, acts of the merchant are generically performed by one or more users. One or more users may include one or more individuals, agents, or both authorized to act on behalf of the merchant. It may be understood that steps throughout which refer to interacting with a user interface and/or performing a step requiring human interaction, refer to a user associated with the merchant. The local location, state location, federal location, or any combination thereof where a regulated product merchant may be situated and operate from may be referred to as the jurisdiction of the regulated product merchant. A jurisdiction associated with a buyer may be referred to as a first jurisdiction, buyer jurisdiction, or both. A jurisdiction associated with a seller may be referred to as a second jurisdiction, seller jurisdiction, or both. The first jurisdiction and second jurisdiction may be the same or different. The first jurisdiction and second jurisdiction may be subject to the same or different jurisdiction-based requirements.

Electronic Transaction System for Selling and Purchasing Regulated Products

The present teachings may be particularly beneficial in providing a transaction system ("system"). The transaction system may be considered a virtual transaction system as buyers and sellers interact with one another via a network such as the Internet. The transaction system may be considered an e-commerce platform for the sale and purchase of regulated products by regulated product merchants. The transaction system may be particularly beneficial in allowing regulated product merchants to both sell and purchase regulated products between one another; provide for an online and electronic marketplace; provide a means of ensuring individual regulated product merchants adhere to regulations regarding the purchase and sale of regulated products; allow for merchants to interact anonymously between one another while in the transaction system, incentivize regulated product merchants to continue use of the transaction system; the like; or any combination thereof. The transaction system may include one or more applications, user interfaces, computing devices, servers, processors, memory storage devices, databases, records, networks, the like, or any combination thereof.

The system may include one or more applications. The application (i.e., "computer program") may function to execute the method of the present teachings, provide an interface for the transaction system, or both. The application may be stored on one or more memory storage devices. The application may comprise one or more computer-executable instructions, algorithms, rules, filters, processes, methods, user interfaces, menus, databases, the like, or any combination thereof. The computer-executable instructions, when executed by a computing device may cause the computing device to perform one or more methods described herein. The application may be downloaded, accessible without downloading (i.e., web-based application), or both. The application may be downloadable onto one or more memory storage media of one or more computing devices. The application may be downloadable from an application store (i.e., "app store"), a website, or both. The application may be accessible via one or more web browsers. The application may be accessible as a website. The application may interact and/or communicate through one or more interaction interfaces, networks, or both. The application may be utilized by one or more computing devices. The application may be utilized on one or more computing devices. The application may also be referred to as a dedicated application.

One or more computing devices may include one or more user interfaces. The one or more user interfaces may function to display information for a user, receive inputs from a user, or both. The one or more user interfaces may be suitable for receiving data (e.g., data inputs) from a user. The one or more user interfaces may include one or more graphical user interfaces ("GUI"), audio interfaces, image interfaces, input interfaces (e.g., keyboard), the like, or any combination thereof. One or more graphical user interfaces may function to display visual data for a user, receive one or more inputs from a user, or both. One or more graphical interfaces may include a page of a web browser, a screen of an application, or both. The one or more graphical user interfaces may include and/or be displayed on one or more screens. The one or more screens may include a screen located on a computing device. The one or more screens may include a screen on a mobile computing device, non-mobile computing device, or both. The one or more graphical user interfaces may include and/or be in communication with one or more user input interfaces, audio interfaces, image interfaces, the like, or any combination thereof. The one or more user input interfaces may allow for receiving one or more inputs from a user. The one or more input devices may include one or more buttons, wheels, keyboards, switches, mice, joysticks, touch pads (i.e., a touch-sensitive area, provided as a separate peripheral or integrated into a computing device, that does not display visual output), touch-sensitive monitor screens, microphones, the like, or any combination thereof. The one or more input devices may be integrated with a graphical user interface (e.g., touchscreen). An audio interface may function to project sound to a user and/or receive sound from a user. The audio interface may include audio circuitry, one or more speakers, one or more microphones, the like, or any combination thereof. An image interface may function to capture, receive, display, transmit, or any combination thereof one or more images. An image interface may include one or more cameras. A user interface may function to display and/or navigate through one or more menus of the application.

One more user interfaces may include a plurality of user interfaces. A plurality of user interfaces may be displayed on a single computing device, a plurality of computing devices, or both. A plurality of user interfaces displayed on a single computing device may include different pages and/or screens of the application. A plurality of user interfaces displayed across a plurality of computing devices may include different instances of the application (e.g., different users logged on, different devices connecting to the application). A plurality of user interfaces displayed on a plurality of computing devices may allow for a plurality of users to interact with the system at differing locations. A plurality of user interfaces displayed on a plurality of computing devices may allow for a plurality of users representing a plurality of merchants to interact with the system simultaneously, from differing locations, or both. A plurality of user interfaces may include at least a first user interface and a second user interface. A first user interface may be part of a first computing device. A first computing device may be located in a first merchant at a first jurisdiction. A second user interface may be part of a second computing device. A second computing device may be located in a second merchant in a second jurisdiction. Each user interface may be associated with or accessible by a user, user account, merchant, merchant account, pharmacy, pharmacy account, the like, or a combination thereof.

One or more user interfaces may include one or more log-in pages, registration pages, profile pages, dashboard pages, posting pages, marketplace pages, virtual shopping cart pages, watchlist cart pages, the like, or any combination thereof. One or more user interfaces may include or be similar to the screen print diagrams disclosed in U.S. patent application Ser. No. 12/693,573, incorporated by reference herein in its entirety. The screen print diagrams may be similar to or the same as one or more pages, screens, or both as described herein. One or more user interfaces may provide visual representations of the data entries stored within one or more databases. One or more user interfaces may be associated with one or more databases. One or a plurality of databases may automatically populate one or more associated user interfaces.

One or more user interfaces may include a graphical user interface which is a registration page. One or more registration pages may allow for a user and/or merchant to register with the transaction system, create authenticating (e.g., log-in) credentials, and the like. A registration page may include a plurality of data fields for receiving data inputs and/or entries. A registration page may receive one or more data inputs and/or entries which populate one or more merchant databases, such as one or more profile databases, licensing databases, banking databases, the like, or a combination thereof. A registration page may include one or more data fields which correspond to one or more data fields in the one or more merchant databases. A registration page may populate one or more databases which then populate one or more profile pages. One or more data entries into one or more registration interfaces may include: a National Provider Identifier (NPI) number, National Council for Prescription Drug Programs (NCPDP) number, legal business name, alternative business name, address of the merchant (e.g., street address, suite, city, state, zip code), phone number, fax number, first name and/or last name of a contact (e.g., owner, manager, pharmacist, etc.), phone number for a contact, email address for a contact, password for a contact, or any combination thereof.

One or more user interfaces may include a graphical user interface which is a posting page. A posting page may function to provide a visual summary of all available regulated products available for sale by a merchant (e.g., acting in the selling capacity, seller). A posting page may include no products listed thereon (e.g., seller does not have any products available for sale), a single product listed thereon (e.g., seller has only a single product for sale, or seller is only viewing one product per page at a time), or a plurality of products listed thereon. A posting page may include a plurality of regulated products available for sale by the merchant. A posting page may include some or all of the regulated products available for sale by a merchant. Listing all of the regulated products available for sale by a merchant on a single posting page can be particularly useful in that a user can avoid opening other pages. A posting page may provide a visual of all regulated products part of an inventory database and corresponding with the merchant to which the user is associated with. A posting page may provide a visual representation of an inventory database. A posting page may display rows and columns. A row on the posting page may be associated with a record in the inventory database. A column on the posting page may be associated with a specific data type in an inventory database. A row on a posting page may be referred to as a posting line. A posting page may divide out the regulated products into individual posting lines. Each posting line may be associated with a single type of regulated product sold by the merchant. Each posting line may include a single or a plurality of descriptive entries. The descriptive entries may be associated with one or more descriptive fields in an inventory database. One or more descriptive fields may include the columns and/or data types in an inventory database. One or more descriptive entries may refer to the data of a descriptive field. One or more descriptive fields may refer to the header and/or label of a column, a field for data entry in a posting line or page, or both. Descriptive entries and/or fields may include any descriptive data type associated with a regulated product. Descriptive entries and/or fields may include: a product image, regulated product name (e.g., pharmaceutical name for a pharmaceutical), serial number, national drug code (NDC) number, lot number, expiration date, packaging type, available quantity, price, discount type, modification date, the like, or a combination thereof. A posting line may also include available actions by the user for the specific regulated product within a posting line. Available actions may allow for a user to edit and/or delete the information of the regulated product in a posting line. While some of the examples herein with reference to the inventory database assume the database is a row-oriented database, similar relationships may be established with a column-oriented database.

A posting page, posting line, or both may include one or more descriptive entries and/or fields. One or more descriptive fields may be limited to one or more pre-determined datatypes for data entry by a user. One or more pre-determined datatypes may allow for the entered data to be correctly recognized and input into one or more inventory databases. One or more pre-determined datatypes may allow for a plurality of users across a plurality of merchants to use common datatypes as one another. One or more pre-determined datatypes may include: image files, file sizes, alphanumeric cases, uppercase, lowercase, numerical only, dates, packaging type, form type, the like, or any combination thereof. Some of the pre-determined datatypes may be automatically provided by dropdown menus, pop-up windows, the like, or a combination thereof.

A product image entry may allow for one or more image file types and images. For example, the product image entry may allow for one or a plurality of images to be entered into the product image descriptive field. A product image entry may allow for 1 or more, 2 or more, or even 3 more images. A product image entry may allow for 10 or less, 8 or less, or even 6 or less images. For example, a product image entry may allow for up to 3 images. Images may include stock images. Stock images may be automatically received from one or more product databases. Stock images may be considered images which are available online, not prepared by the merchant, or both. Images may include user uploaded images. A user may upload one or more actual images, such as to show the condition of packaging. An actual image may be a photograph taken by the user, or another representative of a merchant, of the regulated product being offered for sale and uploaded onto their computing device. For example, three images may include one stock image and two user uploaded images. Images may be limited to specific image file types. Image file types may include jpeg, png, gif, tiff, ps, pdf, eps, ai, indd, raw, the like, or a combination thereof. The system may convert an image file type from one exemplary image file type to another before storing. For example, the system may convert all image file types to png format before storing. Images may be limited to a maximum file size. The product image may have a size restriction with respect to the size of the image file. A size restriction may function to control and limit the amount of memory utilized by the inventory database in one or more storage databases. A size restriction may be about 1 MB or greater, 5 MB or greater, or even 10 MB or greater. A size restriction may be about 100 MB or less, 50 MB or less, or even 25 MB or less. For example, a size limitation for an image may be about 10 MB.

A lot number entry may be limited to alphanumeric entries. This allows for lot numbers to be restricted to industry standards for lot numbers of regulated products. The alphanumeric entries may be limited to uppercase or lowercase. The alphanumeric entries may allow for both upper and lowercase entries. The system, upon receiving a lot number entry, may automatically convert the lot number entry to a restricted datatype. For example, if a user types in a lowercase letter within a lot number field on the user page, the system may automatically convert to uppercase.

An expiration date entry may be limited to date entries. By limiting to a date entry, the system may be able to automatically format all of the received expiration dates within the inventory database into a common date format. The date entry may be possible via a calendar pop-up window, manual entry, or a combination thereof. The date entry may allow only for dates in the future. The date entry may disable entry of dates within the current month and/or previous months. By preventing past dates or even dates in too close of proximity to the present date, the transaction system may prevent regulated products that are already expired or close to expiring from being sold within the transaction system.

A packaging type entry may be limited to pre-determined package types. The packaging type entry may allow for selection of the type of package based on whether or not the regulated product is a full or partial package, package design, the size of package, or a combination thereof. A package design may refer to the style of packaging. A package design may include one or more ampoules, vials, blister packs, bottles, sachets, syringes, cartons, the like, or any combination thereof. The package design may refer to the package in which individual products (e.g., doses) are located, a number of products, or both. For example, a carton may include a plurality of vials. If the packaging type entry is selected as a full package, the system defaults to the known packaging design for that product. The known packaging design may be the packaging design used by a wholesaler and/or manufacturer of the product prior to initial retail. The known packaging may be found in a product database. If the packaging type entry is selected as a partial package, a user may be able to select a packaging design the regulated product may be delivered in to the buyer. If the packaging entry is selected as a partial package, a user may be able to enter in a numerical value, in addition to selecting a packaging design. A numerical value may indicate the size and/or volume of the package (i.e., not the quantity of regulated product).

An available quantity entry type, price entry type, or both may be limited to numerical entries. By limiting an available quantity entry type, price entry type, or both this helps reduce the number of typographical errors by users, provides for a common value type within an inventory database, or both. A numerical entry entered within the price entry field may be converted and/or recognized as a numerical monetary datatype. The transaction system may help keep pricing of regulated products competitive by displaying a marketplace comparison table. Upon a user selecting the price data entry field or selecting another input, such as an icon near the price data entry field, a marketplace comparison table may automatically pop up. A marketplace comparison table may include a table which shows the average, low, and high prices in the transaction system, such as within the inventory database, for the same regulated product available for sale by other merchants. The marketplace comparison table allows for a user to determine a price based with the knowledge of what others are pricing the same regulated product for.

The posting page may include a search tool and/or one or more search filters. The search tool and/or one or more search filters may allow for a user of a merchant to search the regulated products that the same merchant has available for sale. The search tool may allow for alphanumeric entries, nonalphanumeric entries, or both. One or more search filters may be associated with one or more descriptive fields. A search filter will automatically filter for any posting line having a descriptive entry which matches the input in the search tool. Upon filtering via the search tool and/or search filter, the posting page may display the results from the search filter.

The posting page may include an away mode option. The away mode option may be particularly useful if one or more users may be away and unable to interact with other merchants via the transaction system, such as during a vacation, weekend, or emergency. An away mode option allows for a user to remove their attention from the transaction system without being concerned about one or more ratings being impacted, such as a confirmation rating. An away mode option, when enabled, may automatically hide and/or remove regulated products from the marketplace page sold by a user and/or merchant who activated the away mode. An away mode option may allow for a user to prevent any notifications from the transaction system. A user may select the away mode from the posting page. An away mode may be in the form of a user input, such as a toggle switch, check box, radio button, and the like. An away mode may be able to be turned off or on. An away mode option may even allow for entering of dates for a user to automatically enter into away mode, exit away mode, or both.

The posting page may provide for an export function. The export function may allow for a user of a merchant to download a plurality of regulated products the merchant has available for sale for offline reference. An export function may export a posting page, or the inventory displayed therein, into one or more file formats. One or more file formats may be one or more electronic spreadsheet file types. One or more file formats may be Microsoft Excel, Word, PDF, the like, or any combination thereof. Upon export, each posting line may converted into a row within table. Upon export, each descriptive field may be associated with a column. Upon export, descriptive field names may be converted into headers of the table.

One or more user interfaces may include a graphical user interface which is a marketplace page. A marketplace page may allow for a user associated with a marketplace to search and see the inventory available for sale by other merchants in the transaction system, see the inventory available for sale within the inventory database, or both. A marketplace page may automatically display to the buyer one or more regulated products from available inventory which comply with jurisdiction-based rules of both the merchant in the buying capacity (e.g., buyer) and the merchant in the selling capacity (e.g., seller). The marketplace page may display one or more posting lines, search tools, search filters, the like, or a combination thereof. The marketplace page may provide a graphical user interface displaying the content within an inventory database. The marketplace page may display similar information about one or more regulated products as a posting page. The marketplace page may display all regulated products within an inventory database, only regulated products which mean one or more search criteria, or both. The marketplace page may display each regulated product available for sale in a posting line. A posting line may include one or more descriptive entries with data specific to the regulated product within the posting line. A posting line within a marketplace page may provide user inputs for selecting one or more regulated products for purchase, adding to a wishlist, adjusting a quantity for purchasing, the like, or any combination thereof. A marketplace page may be formatted to only show a limited quantity of posting lines (e.g., 10 posting lines per page) or allow for an unlimited amount of posting lines on the single page. It may be beneficial to provide for an unlimited amount of posting lines that a user can scroll through via their graphical user interface, as opposed to multiple pages showing a limited quantity. Users may be more prone to scroll through a single page as opposed to opening multiple pages to view regulated products available for sale.

The system may include one or more computing devices. The one or more computing devices may function to allow a user to interact with an application; cooperate with other computing devices; execute one or more computer-executable instructions; receive and/or transmit one or more data entries (e.g., data signals); convert one or more data signals to data entries; retrieve one or more data entries, computer-executable instructions, or both from one or more storage devices; or any combination thereof. The one or more computing devices may include and/or be in communication with one or more processors, storage devices, servers, networks, user interfaces, other computing devices, printers, the like, or any combination thereof. The one or more or more computing devices may be in communication via one or more interaction interfaces (e.g., an application programming interface ("API")). The computing device may include one or more personal computers (e.g., laptop or desktop), mobile devices (e.g., mobile phone, tablet, smart watch, laptop, etc.), or any combination thereof. A single user and/or merchant may be able to access the application through one or a plurality of computing devices. The computing device may include or be in communication with one or more point-of-sale ("POS") systems. One or more computing devices may include a single or a plurality of computing devices. A plurality of computing devices may be located within a same and/or separate regulated product merchant locations. One or more computing devices may be accessible by a single pharmacy, pharmacy account, and/or user account. A plurality of computing devices may include at least a first computing device and a second computing device. A first computing device may be located separate from a second computing device. For example, a first computing device may be located at and/or associated with a first jurisdiction first regulated product merchant, first pharmacy, first pharmacy account, first user account, buyer, the like, or a combination thereof. For example, a second computing device may be located at and/or associated with a second jurisdiction, second regulated product merchant, second pharmacy, second pharmacy account, second user account, seller, the like, or a combination thereof.

The system may include one or more servers. One or more servers may function to transmit, receive, store, process, convert, or any combination thereof data from one or more applications, computing devices, etc. to one or more other servers, browsers, computing devices, and/or the like. The one or more servers may function to complete one or more processes of one or more applications. The one or more servers may function to execute one or more computer-executable instructions according to the method of the present disclosure. The one or more servers may function to receive input from and/or transmit output to the one or more applications. The one or more servers may include one or more physical servers, virtual servers, or a combination of both. The one or more servers may be non-transient. One or more servers may include one or more local servers, remote servers, or both. The one or more servers may include one or more emails servers, web servers, or both. The one or more servers may include one or more motherboards, processors, storage devices, drives, communication modules, the like, or any combination thereof.

The system may include one or more processors. The one or more processors may function to analyze one or more signals and/or data from one or more user interfaces, computing devices, memory storage devices, databases, or any combination thereof; convert one or more signals to data suitable for analysis and/or saving within a database (e.g., data conversion, data cleaning); or a combination thereof. The one or more processors may be located in one or more user interfaces, computing devices, the like, or any combination thereof. The one or more processors may or may not be cloud-based (e.g., remote from other portions of the system). One or more processors may include one or a plurality of processors. One or more processors may be in communication with one or more other processors. The one or more processors may function to process data, execute one or more computer-executable instructions to analyze data, or both. Processing data may include receiving, transforming, outputting, executing, the like, or any combination thereof. One or more processors may be part of one or more hardware, software, or any combination thereof. One or more hardware processors may include one or more central processing units, multi-core processors, front-end processors, the like, or any combination thereof. The one or more processors may be non-transient. The one or more processors may be referred to as one or more electronic processors. The one or more processors may convert data signals to data entries to be saved within one or more storage devices. A data signal may include a signal associated with an input from a user interface. A data entry may include an entry displayed on a user interface, stored within one or more databases, or both. For example, a user may input a data entry on a user interface, a processor may understand the data entry as a data signal, transmit the data signal to a database, and convert the data signal into a data entry within the database. The one or more processors may access one or more algorithms, processes, and/or methods to analyze one or more data entries and/or data signals. The one or more processors may execute one or more computer-executable instructions. The one or more processors may access and retrieve (e.g., automatically and/or upon user instruction) one or more computer-executable instructions from one or more memory storage devices (i.e., prior to execution). The one or more processors may automatically execute one or more steps of a method. The one or more processors may access (e.g., automatically and/or upon user instruction) and retrieve one or more data entries from one or more databases.

The system may include one or more memory storage devices (i.e., or alternatively referred to as "electronic memory storage device," "storage device"). The one or more memory storage devices may store data, databases, computer-executable instructions, the like, or any combination thereof. The one or more memory storage devices may include one or more hard drives (e.g., hard drive memory), chips (e.g., Random Access Memory "RAM"), discs, flash drives, memory cards, the like, or any combination thereof. One or more discs may include one or more floppy diskettes, hard disk drives, optical data storage media including CD ROMs, DVDs, the like, or a combination thereof. One or more chips may include ROMs, flash RAM, EPROMs, hardwired or preprogrammed chips, nanotechnology memory, the like, or a combination thereof. The one or more memory storage devices may include one or more cloud-based storage devices. The data stored within one or more memory storage devices may be compressed, encrypted, or both. The one or more memory storage devices may be located within one or more computing devices, one or more servers, one or more processors, one or more user interfaces, the like, or any combination thereof. One or more memory storage devices may be non-transient. One or more memory storage devices may store one or more data entries in a native format, foreign format, or both. One or more memory storage devices may store data entries as objects, files, blocks, or a combination thereof. The one or more memory storage devices may include one or more computer-executable instructions, databases, data entries, the like, or any combination therefore stored therein. The one or more memory storage devices may store data and/or data entries in the form of one or more databases.

One or more computing devices may include one or more databases. The one or more databases may function to receive, store, and/or allow for retrieval of one or more data entries. The data entries may include values associated with one or more detected signals and/or data fields, results from one or more computer-executable instructions, or both. The one or more databases may be located within one or more memory storage devices. The one or more databases may include any type of database able to store digital information. The digital information may be stored within one or more databases in any suitable form using any suitable database management system (DBMS). Exemplary storage forms may include relational databases (e.g., SQL database, row-oriented, column-oriented), non-relational databases (e.g., NoSQL database), correlation databases, ordered/unordered flat files, structured files, the like, or any combination thereof. The one or more databases may store one or more classifications of data models. The one or more classifications may include column (e.g., wide column), document, key-value (e.g., key-value cache, key-value store), object, graph, multi-model, or any combination thereof. One or more databases may be located within or be part of hardware, software, or both. One or more databases may be stored on a same or different hardware and/or software as one or more other databases. One or more databases may be located in a same or different non-transient storage device as one or more other databases. The one or more databases may be accessible by one or more processors to retrieve data entries for analysis via one or more computer-executable instructions. The one or more databases may include one database or a plurality of databases. One database may be in communication with one or more other databases. One or more databases may be connected to one or more other databases via one or more networks, within the same storage medium, or both. The one or more databases may receive and store one or more inputs into the system, outputs from the system, or both. The one or more databases may include one or more merchant account databases, banking databases, user account databases, jurisdiction requirement databases, member rating databases, rewards databases, member status databases, inventory databases, regulated product information databases, wishlist databases, communications databases, the like, or any combination thereof. One or more of the databases may be separate from or integrated with one or more other databases. One or more suitable and/or exemplary databases may include databases similar to the data elements described in U.S. patent application Ser. No. 12/693,573, incorporated herein by reference in its entirety. For example, inventory data may be or may be stored in an inventory database, payment mechanisms data may be or be stored in a banking database, profiles data may be or may be stored in a merchant account and/or user account database, jurisdiction-based rules data may be or may be stored in a jurisdiction-based requirements database, the like, or any combination thereof. Databases not discussed herein in detail but disclosed in U.S. patent application Ser. No. 12/693,573 may be incorporated herein by reference in their entirety.

One or more merchant account databases may function to store one or more accounts associated with one or more regulated product merchants. The one or more merchant account databases may function to store data associated with a merchant to allow for the merchant to partake in a transaction for one or more regulated products using the transaction system. The one or more merchant account databases may include one database or a plurality of databases. A plurality of merchant account databases may include one or more records associated with one another via one or more merchant keys. Any data entry that identifies and differentiates one merchant from another may be used as a merchant key. One or more merchant account databases may include one or more profile databases, licensing databases, banking databases, the like, or any combination thereof. These databases may be separate from one another or consolidated into one or more databases.

One or more profile databases may function to retain contact information, general business information, or both of one or more merchants. One or more profile databases may store a plurality of data entries per merchant including the legal merchant business name, alternative merchant business name, postal address (e.g., street, city, state, country), phone number, fax number, email address, the like, or any combination thereof.

One or more licensing databases may function to store licensing information, be accessible to ensure one or more merchants are adhering to one or more jurisdiction-based rules, or both. One or more licensing databases may store data entries per merchant associated with one or more jurisdiction operation rules, regulatory requirements, the like, or a combination thereof. One or more licensing databases may store data (e.g., electronic documentary evidence) from one or more local, state, and/or federal agencies that a merchant is adhering to local, state, and/or federal regulations. One or more licensing databases may store data entries per merchant associated with one or more licenses; permits; licensing and/or permit numbers; start, renewal, and/or expiration dates of one or more licenses and/or permits, the like, or any combination thereof associated with a merchant. One or more licensing databases may store data entries per merchant associated with one or more business registrations (e.g., state business registration); state licenses; state license number (e.g., number associated with state license); Association of Board of Pharmacy (NABP) number; National Council for Prescription Drug Programs (NCPDP) number; Drug Enforcement Agency (DEA) number; Employer Identification Number (EIN); National Provider Identifier (NPI) number; start, renewal, expiration date, or a combination thereof of any of the preceding; the like; or any combination thereof.

One or more banking databases may function to store payment information, be accessible to provide automated payment methods to facilitate a transaction, or both. One or more banking databases may store one or more data entries associated with a payment receiving method, payment sending method, or both. One or more banking databases may store one or more data entries and/or payment methods, which can be automatically accessed and utilized to complete a transaction within the transaction system. One or more banking databases may store one or more bank account numbers, bank routing numbers, bank names, authorized contacts associated with one or more payment methods, credit and/or debit card numbers, billing information, the like, or any combination thereof. One or more banking databases may be automatically accessed to execute one or more electronic funds transfer systems. One or more electronic funds transfer systems may include an automated clearing house. One or more electronic funds transfer systems may be part of a payment heuristic.

One or more user account databases may function to store information related to one or more user accounts, allow each regulated product merchant to provide for one or a plurality of authorized users, or both. A user account may function to store log-in credentials. The log-in credentials may allow for an individual to sign into the application of the transaction system, allow the individual to act (e.g., sell, resell, and/or purchase) on behalf of the merchant, or both. One or more user account databases may store one or more data entries associated with contact information of one or more individuals. One or more user account databases may store one or more data entries associated with a username, password, first name, last name, phone number, email address, profile photo, role, the like, or any combination thereof. Each merchant account, when initially created, may automatically be provided with a user account, profile, or both. A user account, when initially created, may default to an administrator role for the merchant account. An administrator role may have the ability to create other user accounts and/or invite other individuals to have a user account associated with the merchant. An administrator role may have the ability to suspend one or more user accounts associated with the merchant.

One or more inventory databases may function to store inventory of regulated products available for the sale, resale, purchase, and/or distribution by one or more regulated product merchants. One or more inventory databases may be populated by one or more individuals associated with one or more merchant accounts. One or more inventory databases may be automatically updated upon the sale, resale, purchase, or any combination thereof by one or more merchant accounts. One or more inventory databases may include one or more data entries stored therein associated with one or more regulated products available for sale by one or more merchants. One or more inventory databases may include data fields associated with the descriptive fields of a posting line. One or more inventory databases may have one or more data entries associated with a selling merchant (e.g., merchant posting product for sale or resale), creation date (e.g., date merchant/user added into database), modification date (e.g., date a user may have modified a the entry within the database), national drug code (NDC) number, product name, serial number, lot number, expiration date, discounted price, discount percentage, standard package quantity (e.g., original from wholesaler), current package quantity, quantity of packages and/or partial packages available for sale, a package condition, suitable shipping methods, where purchased from, strength (e.g., quantity of a dose, generally measured in grams or milligrams), packaging design (e.g., box, bottle, vial), form (e.g., oral tablet, liquid, capsule, topical, drops, injection, inhaler, etc.), generic or branded, manufacturer, storage information (e.g., room temperature, refrigerated, etc.). One or more inventory databases may retrieve some data entries from one or more regulated product databases.

One or more regulated product databases may function to store information about a number of known regulated products. The one or more regulated product databases may be part of or in communication with the transaction system. The one or more regulated product databases may store one or more records associated with and/or provide standard information about regulated products. The one or more regulated product databases may store one or more data entries associated with one or more regulated product identifiers, packaging, manufacturers, form, storage instructions, strength, and the like. The one or more regulated product databases may store one or more data entries associated with a regulated product name, national drug code (NDC) number, strength, packaging type, form, manufacturer name, storage, standard industry price when sold from the manufacturer, the like, or a combination thereof. One or more data entries in one or more inventory databases may function to associate, retrieve, copy, or any combination thereof one or more data entries from one or more regulated product databases. One or more common data entries between the inventory database and the regulated product database may be used to automatically associate the two databases. For example, a national drug code (NDC) input into the inventory database may be associated with a national drug code (NDC) in the regulated product database and be used to copy data entries associated with that NDC from the regulated product database to the inventory database, to display data entries from the regulated product database on one or more interfaces, or any combination thereof.

One or more wishlist databases may function to store information about one or more regulated products desired by a merchant. One or more wishlist databases may function to store one or more regulated products unavailable in an inventory database and desired for purchasing by a merchant. One or more wishlist databases may be similar to one or more wishlists in U.S. patent application Ser. No. 12/693, 573, incorporated herein by reference in its entirety.

One or more databases may include one or more incentive databases. One or more incentive databases may store one or more data entries related to one or more member incentives and/or incentive programs of the transaction system. One or more incentive databases may include one or more member rating databases, rewards databases, member statuses, the like, or any combination thereof. One or more member rating databases may store one or more seller and/or buyer ratings given to a merchant, one or more member ratings, data output from a member rating algorithm, the like, or any combination thereof. One or more rewards databases may store one or more current rewards, old rewards, new rewards, total lifetime rewards, data output from a rewards algorithm, the like, or any combination thereof. One or more member statuses may store one or more member statuses of one or more merchants, one or more data outputs from one or more member status algorithms, the like, or any combination thereof. One or more incentive databases may store an identifier associated with each record. The identifier may function to associate the record to a specific merchant, associate the record to a merchant in a merchant database, or both.

One or more jurisdiction requirement databases may function to store one or more jurisdiction-based rules. One or more jurisdiction-based rules may be advantageous to allow for one or more regulated product merchants to conduct a transaction via the transaction system with one or more other regulated product merchants, providing for a method for ensuring confidence that regulated product merchants are following regulations in all jurisdictions involved in a transaction without having to know the jurisdiction-based rules outside of their own jurisdiction, allowing for anonymous transactions via the transaction system without having to know the identity of another regulated product merchant involved in a transaction, or any combination thereof. One or more jurisdiction-based rules may include one or more jurisdiction sale rules, jurisdiction operation rules, or both. Jurisdiction sale rules may include jurisdiction-based rules regarding the sale, resale, distribution, or any combination thereof of one or more regulated products. Jurisdiction operation rules may include jurisdiction-based rules for the operation of one or more regulated product merchants. One or more jurisdiction-based rules may be determined by a jurisdiction in which a regulated product merchant is located. Located may include physically located, location of business incorporation or registration, the like, or any combination thereof. One or more jurisdictions may include the city, county, state, region, country, the like, or any combination thereof. One or more jurisdiction-based rules may be accessible by one or more validation heuristics.

The transaction system may be free of one or more jurisdiction requirement databases. In cooperation with or in lieu of, one or more jurisdiction-based rules may be part of a validation heuristic. As an alternative to a validation heuristic accessing a jurisdiction requirement database to retrieve one or more jurisdiction-based rules to automatically confirm compliance, one or more jurisdiction-based rules may be part of (e.g., programmed into) the validation heuristic itself.

One or more jurisdiction operation rules may function to confirm that one or more regulated product merchants are legally operating per their respective jurisdiction in which they are located. One or more jurisdiction operation rules may be particularly advantageous in automatically ensuring merchants interacting with one another via the transaction system are in compliance with their jurisdiction regulations without the merchants having to verify such compliance outside of the transaction system. For example, merchants interacting within the transaction system can be confident that they are interacting with other merchants that are fully state and federally licensed to complete the sale of a regulated product. One or more jurisdiction operation rules may include one or more active permits and/or licenses for a regulated product merchant to engage in the sale, resale, and/or distribution of regulated products. One or more active permits and/or licenses may include federal, state, and/or local level permits and/or licenses. One or more active permits and/or licenses may include a business registration (e.g., state business registration), state license, state license number (e.g., number associated with state license), Association of Board of Pharmacy (NABP) number, National Council for Prescription Drug Programs (NCPDP) number, Drug Enforcement Agency (DEA) number, Employer Identification Number (EIN), National Provider Identifier (NPI) number, the like, or any combination thereof. One or more jurisdiction sale rules may include one or more requirements by jurisdictions to allow the sale, resale, distribution, or any combination thereof of one or more regulated products from a regulated product merchant to another regulated product merchant, consumer (e.g., patient), or both.

One or more jurisdiction sales rules may function to confirm that a specific transaction of a regulated product within the transaction system may be in compliance with the jurisdictional regulations of each jurisdiction associated with each merchant in a transaction. One or more jurisdiction sales rules may be particularly beneficial in automatically ensuring that each participating merchant is allowed to participate in the transaction for a specific regulated product within the inventory, without each merchant having to know each other's jurisdictional requirements or even identity. One or more jurisdiction sale rules may include one or more participating jurisdiction rules, partial packaging rules, the like, or any combination thereof.

One or more participating jurisdiction rules may include the rules for which merchants a merchant within the transaction system can transact with based on the jurisdiction of each merchant. One or more participating jurisdiction rules may include an all-jurisdictions-prevented rule, all-different-jurisdictions-prevented rule, specific-jurisdictions-prevented rule, all-jurisdictions-permissible rule, or any combination thereof. An all-jurisdictions-prevented rule may require that a merchant in a jurisdiction is unable to partake in a transaction via the transaction system with a merchant from the same and/or any other jurisdiction. An all-different-jurisdictions rule may require that a merchant is unable to partake in a transaction via the transaction system with a merchant from a different jurisdiction. A specific-jurisdictions-prevented rule may require that a merchant in a jurisdiction is unable to partake in a transaction via the transaction system with a merchant from one or more specific jurisdictions. One or more specific jurisdictions may include a city, county, state, and/or country different from the merchant and specifically identified. An all-jurisdictions-permissible rule may allow for the merchant to partake in a transaction with a merchant from any jurisdiction.

One or more partial packaging rules may include rules for which merchants within the transaction system may transact with one another based on a specific condition of a regulated product and jurisdiction of each merchant. The specific condition may include if the quantity of the regulated product within a package is less than the original quantity (e.g., standard packaging quantity), the seal of the package is broken (e.g., the package has been opened), or both. A partial package may refer to a package having less than the original quantity, having a broken seal, or both. One or more jurisdictions may allow for the sale of one or more regulated products in full packages, partial packages, or both to one or more merchants in a same jurisdiction, different jurisdiction, any jurisdiction, or a combination thereof. One or more partial packaging rules may include a no-partial-packaging rule, a no-partial-packaging-from-different-jurisdiction rule, a no-partial-packaging-from-a-specific-jurisdiction rule, an any-partial-packaging-from-any-jurisdiction rule, or any combination thereof. A no-partial-packaging rule may restrict a specific merchant from selling and/or purchasing a regulated product with partial packaging regardless of either merchants' jurisdiction. A jurisdictionno-partial-packaging-from-different rule may restrict a specific merchant from selling and/or purchasing a regulated product with partial packaging from another merchant based on one merchant being from a different jurisdiction than another merchant. A jurisdictionno-partial-packaging-from-a-specific rule may restrict a specific merchant from selling and/or purchasing a regulated product with partial packaging from another merchant based on a specific jurisdiction of either merchant party to the transaction. A partial-packaging-from-any-jurisdiction rule may allow for a merchant to sell and/or purchase a regulated product with partial packaging from any other merchant on the transaction system.

One or more databases may include one or more records. The one or more records may function to store one or more data entries associated with one or more users. A record may include one or more data entries associated with one or more data inputs (e.g., data signals, signals). The one or more signals may be collected via a user interface after an initial log-in of a user upon visiting the application. One or more records may be considered a row within a database. One or more records may include one or more data entries. The one or more data entries may be specific to a data field. A data field may be a column within a database. It is also possible that the records are in column form and the data fields are the rows.

One or more storage mediums may include one or more computer-executable instructions stored therein. One or more computer-executable instructions may function to direct one or more processors to execute one or more methods, algorithms, filters, rules, and/or the like; retrieve data and/or store data within one or more storage mediums (e.g., databases); the like; or any combination thereof. The one or more computer-executable instructions may be automatically initiated based on an input from a user, based on an output from a computer-executable instruction, or both. The one or more computer-executable instructions may be automatically initiated (e.g., based on output from the system), manually initiated (e.g., based on human input), or both. One or more computer-executable instructions may include one or a plurality of: a registration heuristic, posting process, search heuristic, purchase selection heuristic, related product heuristic, validation heuristic, rewards algorithm, member rating algorithm, member status algorithm, the like, or any combination thereof.

The system of the present disclosure may be integrated and/or include one or more networks. two or more computing devices may be in selective communication with one or more networks. The one or more networks may be formed by placing two or more computing devices in communication with one another. One or more networks may include one or more computing devices, communication hubs, processors, databases, servers, memory storage devices, the like, or any combination thereof. One or more networks may be free of and/or include one or more communication hubs (e.g., router, wireless router). One or more computing devices of the system may be directly connected to one another without the use of a communication hub. One or more networks may be connected to one or more other networks. One or more networks may include one or more local area networks ("LAN"), wide area networks ("WAN"), virtual private network ("VPN"), intranet, Internet, cellular networks, the like, or any combination thereof. The network may be temporarily, semi-permanently, or permanently connected to one or more computing devices, or any combination thereof. A network may allow for one or more computing devices to be connected to the computing device to transmit one or more data signals to the one or more other computing devices, receive one or more data signals from one or more other computing devices, or both. The network may allow for one or more computing devices to receive one or more data entries from and/or transmit one or more data entries to one or more storage media. The network may allow for transmission of one or more signals, data entries, instruction signals, computer-executable instructions, or any combination thereof, for processing by one or more processors.

Method for Selling and Purchasing Regulated Products Via an Electronic Transaction System The present teachings relate to a method for selling and purchasing regulated products via an electronic transaction system. The method may be particularly useful in providing an automated process for regulated product merchants to interact with one another for the sale and/or purchase of regulated products via the electronic transaction system according to the present teachings. One or more steps, processes (e.g., heuristics), or both may be completed by one or more users, processors, or both. One or more processors may automatically execute all or a portion of one or more processes. The method may include one or more of the following steps: opening an application, authenticating user credentials, a registration heuristic, a posting process, a search heuristic, one or more validation heuristics, purchase selection heuristic, purchase heuristic, one or more related product heuristics, one or more member incentive heuristics, the like, or any combination thereof.

The method may include opening an application. The application may be opened via one or more computing devices. The application may be opened by one or more users associated with one or more merchants. By opening the application, one or more individuals may be able to access one or more features of the transaction system, execute one or more computer executable instructions, sell and/or purchase one or more regulated products, and the like. The application may be accessible as a preloaded and stored application, a browser, the like, or any combination thereof. Upon opening the application, an individual may be prompted to register, log-in, or may already be logged in.

The method may include authenticating user credentials. To log-in, a user may be prompted for their user credentials. User credentials may include a username, password, the like, or any combination thereof. After a user inputting one or more user credentials, one or more processors may automatically compare the user credentials to one or more user account databases. If the credentials match a record entry, the one or more users may be provided access into the application. If the credentials do not match a record entry, the one or more users may be prevented from further accessing the application.

The method may include a registration heuristic. A registration heuristic may function to allow one or more merchants and/or users to register with the transaction system, create one or more user and/or merchant accounts, ensure one or more merchants are qualified to participate within the transaction system, the like, or any combination thereof. A registration heuristic may include one or more steps of: a user initiating a registration heuristic, a user entering one or more data inputs into one or more registration pages, automatically executing one or more validation heuristics, and automatically authorizing one or more merchant and/or user accounts.

One or more individuals (e.g., users) may initiate the registration heuristic via one or more computing devices, user interfaces, the application, or any combination thereof. One or more merchant accounts may be created by one or more individuals. The individuals may be associated with one or more merchants. The one or more individuals may first access the application. The one or more individuals may open one or more registration pages. The one or more individuals may enter one or more data entries associated with the merchant into one or more registration pages. The one or more data entries may be input into one or more data fields as one or more data inputs. One or more registration pages may include one or more data inputs which correspond with one or more data entries in one or more profile databases, licensing databases, banking databases, the like, or any combination thereof. The transaction system may automatically save the one or more data entries input into the one or more registration interfaces as corresponding data entries in one or more profile databases, licensing databases, banking databases, the like, or a combination thereof. One or more processors of the transaction system may automatically detect the one or more data inputs as one or more data signals, transfer the data signals to one or more databases, convert the one or more data signals into data entries, and store the one or more data entries within the data fields of the database. One or more data entries into one or more registration pages may include one or more business names, contact information, user information, and/or permit and licensing information of a merchant. One or more exemplary data entries into one or more registration pages may include: a National Provider Identifier (NPI) number; National Council for Prescription Drug Programs (NCPDP) number; legal business name; alternative business name; an address of the merchant (e.g., street address, suite, city, state, zip code); phone number; fax number; first name and/or last name of a contact (e.g., owner, manager, pharmacist, etc.); phone number for a contact; email address for a contact; password for the contact; state license; state license number (e.g., number associated with a state license); Association of Board of Pharmacy (NABP) number; Drug Enforcement Agency (DEA) number; Employer Identification Number (EIN); start, renewal, expiration date, or any combination thereof of any of the preceding; the like; or any combination thereof. Once a user has completed entry of the one or more data entries into a registration page, the registration heuristic may initiate one or more validation heuristics, Once a user has completed data entry into a registration page and the data is saved, the one or more data entries may be referred to as a proposed merchant and/or user account.

A registration heuristic may execute one or more validation heuristics. Upon a user completing a registration, one or more processors may automatically execute one or more validation heuristics. The one or more validation heuristics may be executed based on the proposed merchant and/or user account. One or more validation heuristics may include one or more merchant validation heuristics, one or more marketplace validation heuristics, or both. A merchant validation heuristic may be particularly advantageous to ensure a merchant registering with the transaction system is compliant with regulations in place for regulated product merchants and to participate in the sale and/or purchase of regulated products. Automatic execution of a merchant validation heuristic may provide an unconventional approach to ensuring merchants participating in e-commerce transactions are in good-standing with their particular regulatory agencies, remove a burden from individual merchants from verifying the good-standing of merchants in their transaction, and thus allow for the virtual marketplace to be anonymous (i.e., the identities of fellow merchants are not known while searching the marketplace page).

A registration heuristic may include automatically authorizing one or more merchant accounts. The accounts authorized may be those compliant with one or more validation heuristics. Upon determining that one or more proposed merchant and/or user accounts are compliant with one or more validation heuristics, one or more processors may automatically convert the one or more proposed merchant and/or user accounts to one or more authorized merchant and/or user accounts. One or more processors may indicate one or more merchant and/or user accounts as authorized within one or more merchant and/or user account databases. One or more authorized merchant and/or user accounts may be granted permissions within the transaction system to interact with other merchants to purchase and/or sell regulated products. One or more authorized merchant and/or user accounts may be referred to as one or more merchant and/or user accounts.

The method may include a posting process. The posting process may allow for a user to add to and/or update the inventory listing (e.g., inventory database) in the transaction system of available regulated products for sale and/or resale, allow for a user to add and/or edit one or more regulated products the merchant they are associated with has available for sale and/or resale, or both. The posting process may be completed via one or more single product posting pages. Upon adding inventory via a posting process, the date of adding may be automatically added by one or more processors as a creation date of the posting within the inventory database. A creation date may be automatically added as a modification date for a new posting. One or more single product posting pages may provide a view of a single regulatory product a merchant has available for sale. A suitable and exemplary product posting process and single product posting page may be disclosed in U.S. patent application Ser. No. 12/693,573, such as with respect to FIGS. 12a-b, incorporated herein by reference in its entirety. The method may include creating and/or editing one or more postings of available regulated products by a merchant.

The posting process may include opening a posting page. Opening a posting page may allow for a user to view one or more postings a merchant they are associated with has available sale, create and/or edit one or more postings, or both. Upon opening the post page, one or more sorting rules may be applied. One or more sorting rules may include a modification rule, discount rule, or both. A user may initiate opening a posting page. A user may open a posting page via one or more computing devices. A user may open a posting page via the application.

The posting process may include creating and/or editing one or more postings of one or more regulated products by editing one or more descriptive field entries on a posting page. The method may include editing one or more descriptive field entries displayed in a posting line of a posting page. In general, online transaction systems provide for individual product posting creating and editing within single product posting pages (e.g., single item editing in a single item browser view). This presents a technical problem in that it can be cumbersome to load individual pages within an application for quick edits of multiple product postings and maintaining an up-to-date inventory database. Providing for editing of a plurality of posting lines displayed on a single posting page associated with a plurality of regulated products provides a technical solution which simplifies the ability for a user to maintain and upkeep their inventory listings and a quick method of updating one or more inventory databases. The method may include automatically updating an inventory database upon a user editing one or more descriptive field entries in a posting line. A user may be able to edit one or more descriptive field entries displayed on a posting line. By clicking on a descriptive field of a posting line, a user may be prompted to edit a descriptive field. For example, a user may be able to edit a lot number, expiration date, available quantity, price, the like, or any combination thereof. When a user selects a descriptive field in a posting line, the descriptive field may be automatically emphasized. Emphasizing may allow for a user's attention to be easily drawn to the descriptive field they wish to or are editing. For example, when user edits a descriptive field for a posting line, that descriptive field may be highlighted or be provided with a background in yellow. After editing a descriptive field, a user may exit the descriptive field. Exiting may include a user clicking anywhere else on the screen, or other common exit strategies. After the user edits and exits a descriptive field in a posting line, that field may be automatically emphasized to show that it was recently edited. Recently edited may mean, since the user last opened the posting page, within a recent timeframe (e.g., 30 minutes, 1 day, 10 days), or both. For example, after a user edits and exits a descriptive field, that field is highlighted or has a background in green. After a user closes the posting page, navigates to another portion of the transaction system, and/or or the recent timeframe elapses, and then returns to the posting page, the previously edited descriptive fields may automatically return to a common and/or standard, non-emphasized format. The posting page may require a user to save the one or more additions and/or edits, may automatically save upon editing by the user, or both. Saving may mean that one or more processors automatically recognize the changed descriptive fields, convert the data entries to data signals, transfer the one or more data entries to their corresponding database records (e.g., descriptive fields in the inventory database), and save as descriptive entries for their associated records. The posting page may be subject to one or more automatic saving rules. One or more automatic saving rules may be applied while a user is editing one or more descriptive fields. One or more automatic saving rules may automatically save one or more edits at pre-determined time increments without a user initiating a save. One or more automatic saving rules may automatically edit one or more associated data entries in one or more inventory databases, a temporary editing database, or both. One or more pre-determined time increments may include once about every 5 milliseconds or greater, 10 milliseconds or greater, or even 15 milliseconds or greater. One or more pre-determined time increments may include once about every 100 milliseconds or less, 50 milliseconds or less, or even 25 milliseconds or less. For example, edits may be automatically saved every 20 milliseconds.

Opening a posting page may initiate automatic execution of a one or more modification rules. One or more modification rules may function to automatically emphasize recently modified posting lines. One or more modification rules may include one or more modification date sorts, recently modified emphasis rules, or both.

A modification date sort may function such that upon opening a posting page, the one or more regulated products and their associated posting lines may be sorted by their modification date. A modification date may be the most recent date any of the descriptive fields within the posting line associated with the regulated product were created and/or edited. The posting lines may be automatically sorted by modification date in ascending or descending chronological order.

Upon opening the posting page, a recently modified emphasis rule may be automatically executed. One or more recently modified emphasis rules may function to automatically emphasize one or more descriptive fields recently modified and/or not recently modified, as compared to the date upon which the posting page is being viewed (e.g., current date). A recently modified emphasis rule may function to bring attention to regulated products within a posting page that have been available to sale for a longer period of time than desired, may need editing by a user to make the regulated product more attractive for sale, or both. Recently modified may mean over a previously occurring time period or action. An action may mean while the posting page has been open, after the posting page has been viewed a pre-determined number of times (e.g., 5 or less views), the like, or any combination thereof. A previously occurring time period may be over a pre-determined timeframe. A pre-determined timeframe may be 1 day or more, 7 days or more, 30 days or more, 60 days or more, or even 90 days or more. A pre-determined timeframe may be 200 days or less, 150 days or less, or even 100 days or less. For example, a pre-determined timeframe may be about 90 days. If one or more descriptive fields have or have not been edited within the pre-determined time frame, those descriptive fields associated with a posting line may be emphasized. For example, if within the past 90 days, one or more descriptive field of a posting line have not been modified, such as the price, that descriptive field is automatically emphasized. To emphasize the descriptive field, the field may be highlighted, text shown in different color, the like, or any combination thereof. For example, the text in the descriptive field may be shown in red font if not modified within the pre-determined time frame. If one or more descriptive fields have been edited while a user is viewing the posting page, those recently edited descriptive fields may be emphasized. Recently edited descriptive fields may be emphasized such as be showing the modified text in green font.

Opening a posting page may initiate automatic execution of a discount rule. A discount rule may function to being a user's attention to one or more regulated products and their discount, motivate a user to modify a discount such that it is in line with a pre-determined discount value, have product listings which are competitive with other regulated product listings in the inventory database and available by other merchants, or any combination thereof. A discount rule may specifically function to draw attention to one or more regulated products in which a discount may differentiate, be less than, or greater than a pre-determined discount value. A pre-determined discount may be a discount from a base price. A base price may be a wholesale acquisition cost (WAC), an average wholesale price (AWP), an average sales price (ASP), the like, or a combination thereof. A base price may be stored within and/or determined from a regulatory product database, inventory database, transaction history database, an external repository of regulatory product sales information, the like, or any combination thereof. A pre-determined discount value may be 2% or greater, 5% or greater, or even 8% or greater. A pre-determined discount value may be about 20% or less, about 15% or less, or even about 12% or less. For example, a pre-determined discount value may be about 10%. As an example, a discount rule may specifically draw attention to one or more regulated products in which a discount in the discount type may be less than the pre-determined discount value. The discount rule may automatically locate (e.g., place) the posting lines for these regulated products at the top of the regulated product listing on the posting page. A discount rule may automatically override a modification rule. By overriding a modification rule, one or more regulated products having a discount in the discount type less than, or otherwise different from, a pre-determined value, may be displayed at the start (e.g., first) of the posting lines on the posting page. The user may then edit the individual posting line, such as the discount type, by initiating a post editing process. A user may be able to override the discount rule by sorting by one or more descriptive fields on the posting page (e.g., clicking on a descriptive field header). A user may be able to resolve application of the discount rule by editing the discount type to be less than, equal to, or greater than a pre-determined value. For example, a user may be able to resolve application of the discount rule by editing the discount type for any identified regulated products and/or posting lines to be equal to or greater than a pre-determined discount value. One or more posting lines identifies by the discount rule may be automatically hidden from a marketplace page. In other words, if a seller does not update one or more discount types to comply with the discount rule, the associated product may not be placed within the marketplace page for viewing and purchasing by a potential buyer.

The method may include a search heuristic. A search heuristic may allow for a user to search an inventory of regulated products available for sale within the transaction system, automatically apply one or more jurisdiction-based rules, ensure that a user is only seeing regulated products which would allow their associated merchant to comply with jurisdiction-based rules for both their merchant. A search heuristic may include a user opening a marketplace page, automatically applying one or more jurisdiction-based rules (e.g., executing a validation heuristic), filtering and displaying on the marketplace page to a user regulated products within the inventory which are in compliance with one or more jurisdiction-based rules, the user inputting search criteria into a search tool on the marketplace page, filtering and displaying regulated products on the marketplace page which meet both jurisdiction-based requirements and meet the search criteria.

A search heuristic may include a user opening a marketplace page. The marketplace page may allow a user to see and search through available inventory of regulated products available for sale. The user may open the marketplace page via the application. Upon opening the marketplace page, one or more validation heuristics may be automatically executed.

A search heuristic may include automatically applying one or more jurisdiction-based rules. One or more jurisdiction-based rules may be automatically applied via one or more validation heuristics. A search heuristic may include automatically executing one or more validation heuristics, such as one or more marketplace validation heuristics. One or more validation heuristics may include a marketplace validation heuristic, merchant validation heuristic, or both. After opening a marketplace page, prior to displaying one or more posting lines and/or regulated products on a marketplace page, or both, one or more validation heuristics may be automatically executed. One or more validation heuristics may search and identify regulated products available for sale in the inventory database which comply with each of the jurisdiction-based rules applicable to both the buyer (e.g., user viewing the marketplace page) and the seller (e.g., merchants selling products visible to buyer).

A search heuristic may include filtering and displaying to the user on the marketplace page one or more regulated products from the available inventory which are in compliance with one or more jurisdiction-based rules. After execution of one or more validation heuristics, only those regulated products identified as available for sale and in compliance with each of the jurisdiction-based rules applicable to both the buyer and the seller may be filtered from the inventory. The regulated products that are filtered may be then displayed on the marketplace page. By automatically applying one or more validation heuristics, filtering, and displaying only those regulated products which are both available and comply with jurisdiction-based requirements, a buyer is only able to view the inventory which they are able to purchase while remaining in full compliance with regulatory requirements of both the buyer and seller, is able to avoid having to know the identity and/or the jurisdiction-based rules for the seller, and is even able to avoid having to identify and/or know the jurisdiction-based rules applicable to themselves as the buyer interacting with the seller.

A search heuristic may include automatic execution of a recent purchase identification. Some merchants repurchase the same products frequently. A recent purchase identification may function to identify frequently and/or recently purchased products on a marketplace page, place recently purchased products in a prime viewable portion of a marketplace page, or both such that they can be easily found by a user. Upon a user opening a marketplace page, one or more processors may automatically execute a recent purchase identification. A recent purchase identification may determine, from a transaction history, regulated products a merchant and/or user has purchased within a recent timeframe. A recent timeframe may mean one day or greater, one week or greater, or even two weeks or greater. A recent timeframe may mean two years or less, one year or less, six months or less, three months or less, 2 months or less, or even one month or less. A recent purchase identification may automatically emphasize one or more recently purchased regulated products on a marketplace page. Emphasis may include locating the associated posting lines at the start of the marketplace page, highlighting the posting lines in a different color, and/or other emphasizing methods. For example, an entire posting line may be highlighted in a color, such as green. As another example, the posting line of a recently purchased product may be placed as the initial posting line on the marketplace page.

A search heuristic may include a user inputting one or more search criteria into a search tool, one or more user filters, or both on the marketplace page. Search criteria, user filters, and a search tool may allow for the user to quickly look for and identify one or more specific regulated products available for sale within the inventory. The search tool and user filters may be displayed on the marketplace page. Search criteria may include the user input into the user filters, search criteria, or both. One or more user filters may be associated with the descriptive fields of the posting lines, inventory database, or both. The search tool may be able execute a search the descriptive fields of the posting lines, inventory, or both. The search tool may function similar to the search tool of the posting page. A user may be able to input a single or a plurality of desired products for searching. A search tool may be able to search for a single or a plurality of regulated products simultaneously. Upon inputting one or more search criteria, one or more search filters, validation heuristics, or both may be automatically executed.

A search heuristic may include filtering and displaying to the user on the marketplace page one or more regulated products which meet both jurisdiction-based requirements and meet the one or more search criteria. A search heuristic may include automatically executing one or more search criteria filters, validation heuristics, or both upon receiving one or more search criteria from a user. One or more validation heuristics may include one or more marketplace validation heuristics, merchant validation heuristics, or both. One or more search criteria filters may search one or more inventory databases for one or more regulated products which include one or more data entries entered into one or more search filters, search tools, or both by a user. The one or more data entries searched by the search criteria filters may include those of the descriptive fields associated with each regulated product. After searching based on the one or more search criteria, the one or more search filters may identify one or more regulated products which partially or fully match the one or more search criteria provided by a user. One or more validation heuristics may be executed prior to, simultaneous with, and/or after one or more search criteria filters are executed. In other words, the search criteria may only search and filter the regulated products identified as compliant by the one or more validation heuristics (e.g., marketplace validation heuristic), the filtered regulated products identified by the search criteria filter may then be the input into the validation heuristic, or both the results from the search criteria filter and the validation heuristic may be compared to one another with common results being those displayed to a user. After execution of one or more validation heuristics, only those regulated products identified as available for sale and in compliance with each of the jurisdiction-based rules applicable to both the buyer and the seller are filtered from the inventory. The regulated products that are filtered and found as compliant by both the search criteria filter and the validation heuristic may be then displayed on the marketplace page. By applying one or more search criteria filters and validation heuristics, filtering, and displaying only those regulated products which are both available and comply with the search criteria and jurisdiction-based requirements, a buyer is only able to view the inventory which they desire to purchase and are able to purchase while remaining in full compliance with regulatory requirements of both the buyer and seller, is able to avoid having to know the identity and/or the jurisdiction-based rules for the seller, and is even able to avoid having to identify and/or know the jurisdiction-based rules for the buyer interacting with the seller.

The method may include executing a purchase selection heuristic. A purchase selection heuristic may function to allow a user to select one or more regulated products from a marketplace page for purchase, specify a quantity, or both. A purchase selection heuristic may include a user selecting for purchase one or more regulated products displayed on a marketplace page. A user selecting for purchase one or more regulated products may include selecting one or more regulated products on a marketplace page, identifying a quantity of partial and/or full packages desired, or both. A user may select a regulated product by selecting a posting line, selecting an image, selecting a button (e.g., "add to cart"), adding a quantity, the like, or any combination thereof. Upon a user selecting one or more regulated products for purchase and/or selecting a quantity of a regulated product and/or packaging, the purchase selection heuristic may automatically add the regulated product(s) to a user and/or merchant's virtual shopping cart, automatically execute one or more related product heuristics, or both.

The method may include automatic execution of one or more related product heuristics. A related product heuristic may function to identify one or more regulated products related to a selected regulated product for purchase, such as for potential cost savings. The one or more related product heuristics may include executing one or more seller filters, validation heuristics, or both. The one or more related product heuristics may commence by automatically executing a seller filter process. A seller filter process may automatically determine a seller associated with the one or more regulated products chosen by a buyer via the marketplace page, added to a shopping cart, or both. A seller filter process may automatically add one or more seller filters to the one or more search filters on the marketplace page. A user may select to execute one or more seller filters, one or more seller filters may be automatically executed, or both. One or more seller filters may sort through and identify any other regulated products in the inventory database that are being sold by one or more sellers in common with the one or more sellers of a regulated product selected for purchase by a user and/or merchant. One or more seller filters may allow one or more sellers to remain anonymous to a buyer. The seller filter may recognize and find a common seller within the inventory database but not disclose the identity of the seller via the transaction system, marketplace page, or both. One or more validation heuristics (e.g., marketplace validation heuristic) may be executed before, simultaneously, or after the one or more seller filters are executed. The one or more regulated products in the inventory database identified by the seller filter as having a common seller may be identified on the marketplace page. Identified may include only displaying the posting lines with a common seller, emphasizing the posting lines by color, moving the common seller regulated items to a top of the marketplace page, creating as separate marketplace page for the regulated products specific to the seller, or any combination thereof.

The method may include automatic execution of one or more validation heuristics. One or more validation heuristics may function to ensure that a transaction taking place within the transaction system complies with regulations of both the buyer and the seller; allows a buyer and seller to automatically comply with one or more, or all applicable, jurisdiction-based rules without knowing the identity of the other party in the transaction, without knowing the jurisdiction-based rules applicable to either party in the transaction, or both; or combination thereof. One or more validation heuristics may include one or more marketplace validation heuristics, merchant validation heuristics, or both. One or more validation heuristics may be automatically executed upon one or more users registering one or more merchants in the transaction system, upon one or more expiration dates of one or more licenses and/or permits approaching and/or occurring, upon a search heuristic commencing, during a search heuristic, during one or more related product heuristics, the like, or any combination thereof. One or more validation heuristics may automatically execute one or more jurisdiction-based rules. Execution of one or more validation heuristics may include execution of one or more merchant validation heuristics, marketplace validation heuristics, or both.

One or more validation heuristics may include one or more merchant validation heuristics. One or more merchant validation heuristics may function to ensure a merchant is permitted to interact within the transaction system. Executing one or more merchant heuristics include automatically applying one or more jurisdiction operation rules, jurisdiction sale rules, or both. One or more merchant validation heuristics may be automatically initiated upon a user completing a registration heuristic, an expiration date of a license and/or permit approaching and/or occurring, a posting heuristic being executed, a searching heuristic being executed, a purchase selection heuristic being executed, a purchase heuristic being executed, the like, or any combination thereof. One or more merchant validation heuristics may access one or more licensing databases and find one or more data entries associated with a merchant. The merchant validation heuristic may include accessing one or more external licensing databases. One or more external databases may be one or more databases storing licensing and/or permit information therein. The one or more external databases may be managed by licensing agencies for one or more jurisdictions. Accessing one or more external licensing databases may occur over a network, such as the Internet. The merchant validation heuristic may include automatically and/or manually searching for one or more licenses and/or permits within the external license database. Searching may include searching for a license and/or permit credential which matches the one submitted into the registration interface, profile database, or both. Searching may include determining if there is a matching credential within the external licensing database. Searching may include finding the presence of an expiration date for a license and/or permit within the external license database. Searching may include comparing an expiration date to the present date (e.g., date of the searching is completed), determining if the expiration date is prior to, equal to, or after the present date, or any combination thereof. If the searching determines that there is a matching license and/or permit in the external database, an expiration date (if available) is after the present date, or both, then the merchant validation heuristic determines that the merchant is adhering to jurisdiction operation rules for operating as a regulated product merchant, can partake in the transaction system, allows for displaying of regulated products being sold by the merchant to other merchants (e.g., buyer(s)) in the marketplace, allows the merchant to act in the buying capacity in the transaction system and view a marketplace, purchase regulated products from a marketplace, the like, or any combination thereof. if searching determines that one or more licenses and/or permits required by one or more jurisdictions associated with a merchant are missing, expired, or otherwise not complied with, the merchant validation heuristic may automatically transmit one or more notifications to the merchant. The one or more notifications may be transmitted via a communication system within the transaction system. The one or more notifications may inform the merchant of a discrepancy related to one or more licenses and/or permits associated with an account of the merchant.

One or more validation heuristics may include one or more marketplace validation heuristics. One or more marketplace validation heuristics may function to ensure a transaction within the transaction system is adhering to the jurisdiction-based rules of each jurisdiction associated with each merchant taking part in the transaction (e.g., buyer and seller). Executing one or more marketplace heuristics may include automatically applying one or more jurisdiction operation rules, jurisdiction sale rules, or both. One or more marketplace validation heuristics may be automatically initiated upon a user initiating or executing a posting heuristic, a searching heuristic, a purchase selection heuristic, a purchase heuristic, the like, or any combination thereof. One or more marketplace validation heuristics may access one or more jurisdiction requirement databases, one or more merchant databases, one or more inventory databases, the like, or any combination thereof. A marketplace validation heuristic may execute a seller buyer determination step. During a seller buyer determination step, the validation heuristic may determine which merchant is acting in the capacity of buyer and which in capacity of seller. The marketplace validation heuristic may automatically recognize the user logged in and viewing a posting via a marketplace page, a posting not available for sale by the merchant they are associated with, or both is acting in the capacity of buyer. The marketplace validation heuristic may automatically recognize the merchant to whom a posting belongs is the seller. One or more marketplace validation heuristics may automatically determine what jurisdiction each merchant (e.g., buyer and seller) are associated with. One or more marketplace validation heuristics may determine that the buyer and seller are associated with a first jurisdiction and second jurisdiction, respectively. To determine the first and second jurisdiction, a marketplace validation heuristic may access the merchant database, find a record entry associated with the buyer and find a record entry associated with a seller. One or more marketplace validation heuristics may determine if the first jurisdiction and the second jurisdiction are the same or different. One or more marketplace validation heuristics may then find the one or more jurisdiction-based rules applicable to the first jurisdiction and the second jurisdiction. One or more marketplace validation heuristics may use the first and second jurisdiction found from the merchant database to search the jurisdiction requirement database. The marketplace validation heuristic may find one or more record entries associated with the first and second jurisdiction in the jurisdiction requirement database. The marketplace validation heuristic may then apply one or more jurisdiction-based rules, such as one or more jurisdiction sale rules, based on the first and/or second jurisdiction. Jurisdiction sale rules may include application of a participating jurisdiction rule, partial packaging rule, or both. The marketplace validation heuristic may only allow for a transaction meeting each of the applicable jurisdiction sale rules applicable to both the buyer and the seller.

The method may include a purchase heuristic. A purchase heuristic may function to allow a buyer to purchase one or more regulated products, allow for a buyer to pay a seller for one or more regulated products, the like, or any combination thereof. A purchase heuristic may be initiated by a user associated with a merchant. A purchase heuristic may be initiated by a user opening their virtual shopping cart. A virtual shopping cart may display one or more posting lines for one or more regulated products selected by a user for purchase. A purchase heuristic may include executing automatic payment from a buyer to a seller. A purchase heuristic may include automatically executing one or more payment methods. One or more suitable payment methods may be disclosed in U.S. patent application Ser. No. 12/693,573, incorporated herein by reference in its entirety for all purposes.

The method may include one or more member incentive heuristics. The member incentive heuristics may function to incentivize merchants to sell and/or purchase regulated products via the transaction system, continued use of the system, or both. The one or more member incentive heuristics may be automatically executed by one or more processors. The one or more member incentive heuristics may be executed prior to a transaction being completed (e.g., automated payment), upon a user logging into the system, at pre-determined period intervals, the like, or any combination thereof. The one or more member incentive heuristics may include a rewards algorithm, member rating algorithm, member status algorithm, the like, or a combination thereof.

The method may include a rewards algorithm. The rewards algorithm may function to incentivize merchants to sell and/or purchase regulated products via the transaction system, provide a discount to purchases made via the transaction system, correlate a discount to selling and/or purchasing history such that a discount may increase with increased sales and/or purchases via the transaction system, or any combination thereof. The rewards algorithm may automatically determine a discount usable by one or more merchants to purchase regulated products based on their transaction history. The rewards algorithm may be automatically executed. The rewards algorithm may be automatically executed at a pre-determined time interval. A pre-determined time interval may be daily, weekly, monthly, quarterly, or even annually. For example, a rewards algorithm may be automatically executed on the first of the month each month. Some portions of a rewards algorithm may be automatically executed at differing pre-determined periods of time. The rewards algorithm may apply one or more filters, rules, algorithms, or any combination thereof. The rewards algorithm my determine a total current rewards available to a merchant. The one or more rewards rules may include: a period filter, threshold rule, new rewards rule, old rewards rule, current rewards algorithm, lifetime rewards algorithm, the like, or a combination thereof. The rewards algorithm may automatically execute one or more portions of the algorithm simultaneously, subsequent from another, or both.

A rewards algorithm may include a period filter. A period filter may be automatically executed upon execution of a rewards algorithm. A period filter may look to identify (e.g., filter) a merchant's selling history, purchase history, or both within the transaction system occurring over a pre-determined period of time. A selling history, purchase history, or both may include a type, quantity, price, the like, or any combination thereof of regulated products sold, purchased, or both by a regulated product merchant. A pre-determined period of time may be one week or more, two weeks or more, three weeks or more, or even 4 weeks or more. A pre-determined period of time may be annually, biannually, quarterly, or even monthly. The period filter may be automatically executed at the start and/or end of a pre-determined period of time. The period filter may filter the selling history and/or purchase history from the day before the present day (e.g., current day, date of) that the period filter is executed and for the pre-determined period of time. For example, if the pre-determined period of time is monthly and executed on the first of the month, the period filter will filter the merchant's selling and/or purchase history for the entire month prior to the present (e.g., On October 1, filter for history throughout month of September). After application of a period filter, the rewards algorithm may apply one or more rules.

A rewards algorithm may include a threshold rule. A threshold rule may look to identify a threshold value of regulated products sold and/or purchased by a merchant within the transaction system. A threshold rule may be automatically executed simultaneous with and/or after a period filter. A threshold rule may include one or more threshold aggregators, threshold filters, or both. A threshold aggregator may automatically aggregate the quantity, price, type, the like, or any combination thereof of regulated products sold, purchased, or both by a regulated product merchant over a pre-determined period of time, as identified by the period filter. A threshold aggregator may determine an aggregate value of regulated products sold, purchased, or both by each merchant during the pre-determined period of time applied by the period filter. The aggregate value may be an aggregated quantity, monetary value, and/or the like. After determining an aggregated value, a threshold filter may be applied. A threshold filter may identify those merchants, that during the pre-determined period of time, sold and/or purchased an aggregate value at or above the threshold value. For example, a threshold value may be established at $2,500 of regulated products sold and/or purchased over a one-month pre-determined period of time. After determining the merchants that meet or exceed the threshold value over the pre-determined period of time via a threshold rule, the rewards algorithm may move on to a new rewards rule, old rewards rule, or both.

A rewards algorithm may include a new rewards rule. The new rewards rule may apply one or more rewards to one or more merchant accounts, merchants identified by a period filter as being active in the transaction system over pre-determined period of time, merchants identified by threshold rule as meeting or exceeding the threshold value over a pre-determined period of time, or any combination thereof. The new rules rewards rule may provide one or more new reward values to the aggregate value determined during the threshold rule. One or more new reward values may be associated with one or more aggregate values. A new reward value may be a monetary value. The monetary value may be a percentage of the aggregate value. The monetary value may be about 0.1% or greater, 0.3% or greater, or even 0.5% or greater. The monetary value may be about 2% or less, about 1% or less, or even about 0.7% or less. For example, the new reward value may be a reward rate of 0.5% awarded to the aggregate value which is a total monetary value of regulated product purchased and/or sold by a merchant over the pre-determined period of time. Further to the example, if a merchant sold $3,000 in regulated products over one-month period, the merchant account would be assigned a new reward value of $15. Upon determining the new reward value by the new rewards rule, the rewards algorithm may automatically store the new reward value in a rewards database and associate the new reward value with the merchant within the same rewards database. Upon completion of, or simultaneous with, the new rewards rule, the rewards algorithm may apply an old rewards rule.

A rewards algorithm may include an old rewards rule. The old rewards rule may remove one or more rewards from one or more merchant accounts, eliminate expired rewards from total current rewards, prevent merchants from accumulating rewards over an pre-determined period of time, incentive merchants to user rewards within the transaction system and thus incentivize continued use within the transaction system. The old rewards rule may include an old rewards filter, old rewards removal, or both. The old rewards rule may automatically apply an old rewards filter. The old rewards filter may filter rewards assigned to merchants over an earlier pre-determined period of time. The earlier pre-determined period of time may be prior to the pre-determined period of time. The earlier pre-determined period of time may be weeks, months, or even years prior to the pre-determined period of time. The earlier pre-determined period of time may be one month, two months, three months, or even one year prior to the pre-determined period of time. For example, the earlier pre-determined period of time may be two months. After application of the old rewards filter, the old rewards rule may determine an old rewards value. The old rewards value may be an aggregated value of quantity, price, or the like of the rewards assigned to a merchant over the earlier pre-determined period of time. The old rewards value may cooperate with the new reward value to provide a total current rewards value.

A rewards algorithm may include a current rewards algorithm. A current rewards algorithm may function to determine the amount of active rewards associated with a merchant account and available for use by the merchant. The current rewards algorithm may automatically aggregate and/or subtract the old rewards and the new rewards values. The current rewards algorithm may automatically subtract the old rewards from the new rewards value upon completion of both the new rewards rule and the old rewards rule to determine a total current rewards. The current rewards algorithm may automatically store the total current rewards in a rewards database and associate the total current rewards with the corresponding merchant. The total current rewards may be displayed on a user interface associated with the merchant. All or at least a portion of the total current rewards may be applied as payment toward a transaction. For example, when a merchant is acting in the capacity of buyer, the buyer may apply all or a portion of the total current rewards toward a purchase of one or more regulated products. The rewards may be deduced from a cost total prior to completing the transaction. The current rewards total may be automatically updated after completion of a purchase to reflect the use of some or all of the total current rewards during a transaction within the transaction system. In other words, the current rewards total may automatically subtract the amount of rewards used during a transaction upon completion of the transaction and determine an up-to-date current rewards total.

A rewards algorithm may include lifetime rewards algorithm. A lifetime rewards algorithm may function to determine an aggregate rewards value that a merchant has accumulated since they joined the transaction system. A lifetime rewards algorithm may aggregate each new rewards value assigned during each previously occurring pre-determined period of time. A lifetime rewards value determined for a merchant may be stored within a rewards database and associated with the merchant within the database.

The method may include a member rating algorithm. The member rating algorithm may function to determine a member rating for a merchant. The member rating algorithm may function to determine a rating for each merchant based on interactions with other merchants in the system. The member rating algorithm functions to incentivize merchants to cooperate with other merchants, provide timely deliveries of regulated product purchases to a buyer, strengthen a merchant's credibility within the transaction system, reward merchants for positive interactions with one another, encourage interaction with one another in the transaction system, or any combination thereof. The member rating may function to analyze a merchant's behavior in the transaction system, provide a rating based on behavior, or both. Behavior may be when the merchant is acting in the capacity of a buyer, seller, or both. The member rating algorithm may apply one or more buyer algorithms, seller algorithms, or both to determine a member rating. A member rating may be based on one or more cancellation ratings, payment ratings, average seller ratings, confirmation ratings, revision and cancellation ratings, average buyer ratings, delivery ratings, the like, or any combination thereof. The member rating algorithm may weigh all the one or more buyer ratings, seller ratings, or both equally or unequally. The member rating algorithm may determine the member rating by first determining the buyer rating and seller rating, and then averaging the buyer rating and seller rating. The buyer rating may be an average of the one or more buyer sub-ratings. The seller rating may be an average of the one or more seller sub-ratings. The member rating may determine the member rating by averaging each of the buyer sub-ratings and seller sub-ratings.

The member rating algorithm may include one or more buyer algorithms. One or more buyer algorithms may determine one or more buyer ratings, sub-ratings, or both. One or more buyer algorithms may function to analyze the behavior of a merchant in the capacity of a buyer, provide a rating based on purchasing behavior, contribute to the overall member rating, or any combination thereof. One or more buyer algorithms may function to convert a merchant's behavior as a buyer into a numerical representation. A numerical representation may be a percentage, decimal, ratio, integer, the like, or any combination thereof. A merchant's behavior as a buyer may include: cancelled orders, orders with payment rejections, average rating from sellers, the like, or a combination thereof. One or more buyer algorithms may include one or more of a cancelled order sub-algorithm, payment sub-algorithm, average seller rating sub-algorithm, the like, or any combination thereof. A merchant's behavior as a buyer may be objective, subjective, or both. Objective may be based on actual behavior, a number of occurrences, or both. Subjective may be based on the opinion and/or feelings of other merchants within the transaction system. Cancelled orders, orders with payment rejections, and the like, may provide for an objective numerical representation. A seller's average rating may provide for a subjective numerical representation. One or more buyer algorithms may weigh all sub-algorithm ratings evenly or unevenly. For example, objective numerical representations may be assigned a higher weight than subjective numerical representations. As another example, all numerical representations may be equally weighted and averaged. One or more buyer ratings may be equal to or the average of one or more of a cancellation rating, payment rating, average seller rating, the like, or a combination thereof. The individual ratings that make up a buyer rating may be considered buyer sub-ratings. The cancellation rating, payment rating, average seller rating, and/or the like may be considered buyer sub-ratings.

A cancelled order sub-algorithm may determine a cancellation rating. A cancellation rating may be a rating associated with the number of orders a merchant, acting in the capacity of buyer, has cancelled. These cancellations may be at any time during the transaction process, prior to a seller revising an order, after payment and before shipment, the like, or any combination thereof. The cancelled order sub-algorithm may look at the cancellations occurring since the time the merchant joined the transaction system, over a pre-determined period of time (e.g., 6 months, 1 year, 3 years, 5 years), or the like. The cancelled order sub-algorithm may compare the number of cancelled purchased orders by the merchant to the total number of purchased orders and convert to a fraction, percentage, or the like. For example, a merchant who has purchased 100 orders since joining the transaction system and cancelled 4 purchased orders without any seller revisions to the orders, may have a cancellation rating of 0.96, 96%, or both.

A payment sub-algorithm may determine a payment rating. A payment rating may be a rating associated with the number of payments by a merchant rejected by the transaction system. A rejected payment may be any payment which is declined. A payment may be declined for insufficient funds, expired payment information, incorrect payment information, the like, or any combination thereof. The payment sub-algorithm may look at the number of rejected payments occurring since the merchant joined the transaction system, over a pre-determined period of time, or the like. A pre-determined period of time may be the same or different pre-determined period of time as that of the cancellation sub-algorithm. The payment sub-algorithm may compare the number of payment rejections to the total number of payment attempts, purchased orders, accepted payments, the like, or any combination thereof. The payment sub-algorithm may then take the comparison and convert to a fraction, percentage, or the like to provide for the payment rating. For example, a merchant who has attempted making 50 payments since joining the transaction system, has had 2 payments rejected, and had 48 payments with success, may have a payment rating of 0.94 or 94%.

An average seller rating sub-algorithm may determine an average seller rating. An average seller rating may be associated with a rating of a merchant by other merchants in the selling capacity who have interacted with a merchant in a buying capacity. After completion of a transaction within the transaction system, a seller may be provided the opportunity to rate the buyer. The transaction system may automatically display a seller rating input on the user interface. The seller rating input may provide for a visual representation of a numerical rating, a numerical representation, the like, or a combination thereof. A visual representation may provide for visual icons associated with numerical rating. Visual icons may include stars (e.g., 5 stars=100%), face emoticons (e.g., facial expressions associated with ratings), thumbs up and down, the like, or any combination thereof. A numerical representation may be provided as a user number input (e.g., a user enters an integer, such as "98" to mean 98%), a sliding scale (e.g., a user slides a scale to define a numerical rating), a list and range selection (e.g., a user is presented with a list of ranges to choose from, such as 70-80%, 80-90%, 90-95%, and 95-100%), the like, or a combination thereof. The average seller rating sub-algorithm may look at the average ratings of a merchant in a buying capacity provided by other merchants while in the selling capacity since the merchant joined the transaction system, over a pre-determined period of time, or both. A pre-determined period of time may be the same or different pre-determined period of time as that of the cancellation sub-algorithm, payment sub-algorithm, or both. The average seller rating sub-algorithm aggregate all of the seller ratings, average all of the seller ratings, or both. The average seller rating sub-algorithm may or may not account for merchants in the selling capacity that have not provided a seller rating. By not accounting for these missing or unprovided ratings, a seller rating is not negatively impacted by a merchant deciding not to provide a rating (e.g., such as when in a hurry to complete a transaction). The average seller rating sub-algorithm may then take the average seller ratings and convert to a decimal or percentage. For example, a merchant may have a 95% average seller rating after averaging all of the individual seller ratings given to the merchant since the merchant joined the transaction system.

The member rating algorithm may include one or more seller algorithms. One or more seller algorithms may determine one or more seller ratings. One or more seller algorithms may function to analyze the behavior of a merchant in the capacity of a seller, provide a rating based on selling behavior, contribute to the overall member rating, or any combination thereof. One or more seller algorithms may function to convert a merchant's behavior as a seller into a numerical representation. A numerical representation may be a percentage, decimal, ratio, integer, the like, or any combination thereof. A merchant's behavior as a seller may include: confirmation history, revision history, cancellation history, average delivery time of regulated products, average rating from buyers, the like, or a combination thereof. One or more seller algorithms may include one or more of a confirmation sub-algorithm, revision and cancellation sub-algorithm, an average buyer rating sub-algorithm, a delivery algorithm, the like, or any combination thereof. A merchant's behavior as a seller may be objective, subjective, or both. Objective may be based on actual behavior, a number of occurrences, or both. Subjective may be based on the opinion and/or feelings of other merchants within the transaction system. Confirmation history, the number of revised and cancelled order history, delivery timing, and the like, may provide for an objective numerical representation. A buyer's average rating may provide for a subjective numerical representation. One or more seller algorithms may weigh all sub-algorithm ratings evenly or unevenly. For example, objective numerical representations may be assigned a higher weight than subjective numerical representations. As another example, all numerical representations may be equally weighted and averaged. One or more seller ratings may be equal to or the average of one or more of a confirmation rating, revision and cancellation rating, delivery rating, average buyer rating, the like, or a combination thereof. The individual ratings that make up a seller rating may be considered seller sub-ratings. The confirmation rating, revision and cancellation rating, delivery rating, average buyer rating, and/or the like may be considered seller sub-ratings.

A confirmation sub-algorithm may determine a confirmation rating. A confirmation rating may function to motivate a merchant to keep their available inventory (e.g., postings) up-to-date within the transaction system, quickly interact with buyers, or both. A confirmation rating may be associated with how often a merchant acting in the capacity of a seller (e.g., seller) confirms an order from a merchant acting in the capacity of a buyer (e.g., buyer), how quickly a seller confirms an order from the buyer, or both. The confirmation sub-algorithm may look at confirmations from a merchant since the merchant joined the transaction system, over a pre-determined period of time (e.g., 6 months, 1 year, 3 years, 5 years), or the like. A pre-determined period of time may be the same or different as one used in the buyer rating algorithm. The confirmation sub-algorithm may determine the total number of purchase requests by a buyer received by a seller, the number of confirmations provided by the seller, the time elapsed between a purchase request being made by the buyer and the confirmation provided to the seller, or any combination thereof. Different levels of time elapsed between the purchase request and the confirmation may be associated with numerical representations. For example, 0 minutes up to 1 hour may be associated with 100%, 1 hour to 2 hours may be associated with 98%, 2 hours to 3 hours may be associated with 95%, 3 hours to 5 hours with 90%, and so forth. The confirmation sub-algorithm may determine an individual confirmation rating per transaction, purchase request, or both within the transaction system. The confirmation sub-algorithm may aggregate, average, or both the individual confirmation ratings to yield a confirmation rating. For example, a merchant in the capacity of seller has confirmed purchases with a 98% average individual confirmation rating and thus has a 98% confirmation rating.

A revision and cancellation sub-algorithm may determine a revision and cancellation rating. A revision and cancellation rating may include a rating associated with the number of orders a merchant, acting in the capacity of seller, has revised. Revisions may include changing an order, cancelling an order, or both. Changing an order may include proposing a new quantity, changing a form of a regulated product (e.g., tablet to capsule, capsule to liquid), changing a brand of a regulated product within the purchase order, removing a regulated product from a purchase order having multiple regulated products therein, the like, or any combination thereof. These revisions may be at any time during the transaction process, after receiving a purchase request from a buyer, after payment and before shipment, after shipment, the like, or any combination thereof. The revision and cancellation sub-algorithm may look at the revisions occurring since the time the merchant joined the transaction system, over a pre-determined period of time (e.g., 6 months, 1 year, 3 years, 5 years), or the like. The pre-determined period of time may be the same or different as that of the confirmation sub-algorithm. The revision and cancellation sub-algorithm may compare the number of purchase orders revised by the merchant to the total number of purchased orders received by the merchant and convert to a fraction, percentage, or the like. For example, a merchant who has received 100 purchase orders since joining the transaction system, changed 2 of those orders and cancelled 3 of those orders, may have a revision and cancellation rating of 0.95 or 95%.

An average buyer rating sub-algorithm may determine an average buyer rating. An average buyer rating may be associated with a rating of a merchant by other merchants in the buying capacity who have interacted with a merchant in a selling capacity. After completion of a transaction within the transaction system, a seller may be provided the opportunity to rate the buyer. Completion of a transaction may be after payment being processed, after an order is cancelled by a seller, after delivery of a regulated product from a purchase order to a buyer, the like, or any combination thereof. The transaction system may automatically display a buyer rating input on the user interface. The buyer rating input may provide for a visual representation of a numerical rating, a numerical representation, the like, or a combination thereof. A visual representation may provide for visual icons associated with numerical rating. Visual icons may include stars (e.g., 5 stars=100%), face emoticons (e.g., facial expressions associated with ratings), thumbs up and down, the like, or any combination thereof. A numerical representation may be provided as a user number input (e.g., a user enters an integer, such as "98" to mean 98%), a sliding scale (e.g., a user slides a scale to define a numerical rating), a list and range selection (e.g., a user is presented with a list of ranges to choose from, such as 70-80%, 80-90%, 90-95%, and 95-100%), the like, or a combination thereof. The average buyer rating sub-algorithm may look at the average ratings of a merchant in a selling capacity provided by other merchants while in the buying capacity since the merchant joined the transaction system, over a pre-determined period of time, or both. A pre-determined period of time may include the same or different pre-determined period of time as that of the confirmation sub-algorithm, revision and cancellation sub-algorithm, or both. The average buyer rating sub-algorithm may aggregate all of the buyer ratings, average all of the buyer ratings, or both. The average buyer rating sub-algorithm may or may not account for merchants in the buying capacity that have not provided a buyer rating. By not accounting for these missing or unprovided ratings, a buyer rating is not negatively impacted by a merchant deciding not to provide a rating (e.g., such as when in a hurry to complete a transaction). The average buyer rating sub-algorithm may then take the average buyer ratings and convert to a decimal or percentage. For example, a merchant may have a 98% average buyer rating after averaging all of the individual buyer ratings given to the merchant since the merchant joined the transaction system.

A delivery sub-algorithm may determine a delivery rating. A delivery rating may be associated with how quickly a seller prepares a purchased order for delivery, sends a delivery to a buyer, or both. A delivery rating may reflect the actions of the seller and not a delivery method (e.g., shipment method, shipping entity). The delivery sub-algorithm may look at the number of deliveries from a merchant since the merchant joined the transaction system, over a pre-determined period of time (e.g., 6 months, 1 year, 3 years, 5 years), or the like. A pre-determined period of time may be the same or different as one used in the confirmation sub-algorithm, revision and cancellation sub-algorithm, average buyer rating sub-algorithm, the like, or a combination thereof. The delivery sub-algorithm may determine the total number deliveries sent by a seller, the total number of time (e.g., hours, days) elapsed between completing an online transaction in the transaction system and sending the delivery to the buyer, the total time elapsed between completing an online transaction in the transaction system and preparing the regulated product for shipping, or any combination thereof. Different levels of time elapsed between the online transaction being completed and preparing and/or shipping the purchased regulated product may be associated with numerical representations. For example, less than one day may be associated with 100%, one day may be associated with 99%, two days may be associated with 95%, and so forth. The delivery sub-algorithm may determine an individual delivery rating per transaction, purchase request, or both within the transaction system. The delivery sub-algorithm may aggregate, average, or both the individual delivery ratings to yield a delivery rating. For example, a merchant in the capacity of seller has confirmed purchases with a 95% average individual confirmation rating and thus has a 95% confirmation rating.

The method may include a member status algorithm. The member status algorithm may function to determine a membership status of one or more merchants, provide incentives to one or more merchants based on their membership status, or both. A member status algorithm, member status, or both may be particularly useful in assigning incentives (e.g., benefits) to merchants based on their transactions in the transaction system and thus incentivizing continued use of the transaction system. Exemplary benefits may include: a different transaction limit, shipping incentives, fee discounts, purchase minimums, transaction fees, early wishlist notifications, pickup fees, the like, or any combination thereof. Benefits may be automatically applied within the transaction system based on the member status of a merchant. A member status algorithm may be executed periodically, upon a user of the merchant logging into the transaction system, upon a merchant completing a transaction in the transaction system, or any combination thereof. Periodically may include daily, weekly, monthly, quarterly, or even annually. The member status algorithm upon determining a member status may automatically display a member status on a user interface of the transaction system. The user interface may include a dashboard, marketplace page, posting page, profile page, the like, or any combination thereof. The member status algorithm may include a transaction sub-algorithm, status filter, status rule, status assignment, the like, or any combination thereof.

A member status algorithm may include a transaction sub-algorithm. A transaction sub-algorithm may function to determine the number of transactions associated with a merchant. A transaction sub-algorithm may automatically access a merchant's transaction history. A transaction sub-algorithm may determine how many transactions a merchant has had over a pre-determined time period. Transactions may include sales, purchases, or both. A pre-determined time period may include one week or more, two weeks or more, or even three weeks or more. A pre-determined time period may include five years or less, three years or less, one year or less, three months or less, or even one month or less. A pre-determined time period may be from the current day (e.g., the day the member status algorithm is executed), from a periodically occurring day (e.g., the first of each month), the like, or a combination thereof. For example, a pre-determined time period may be monthly for the month before the first day of the present month. Transactions during the pre-determined time period may be presented as an actual total number, an average, or even peak, or low of transactions during the pre-determined time period. For example, a pre-determined time period may be quarterly for the three months prior to the first day of the present month. In this example, the number of transactions may be represented as an average number of transactions per month.

A member status algorithm may include automatically applying one or more status filters. The one or more status filters may function to sort the one or more merchants into one or more status groups based on the outcome of the transaction sub-algorithm. For example, the one or more merchants may be sorted into a first group, second group, third group, fourth group, and so forth based on their total and/or average transactions over the pre-determined time period. A first group, second group, third group, fourth group, and so forth may include a platinum group, gold group, silver group, bronze group, respectively. Each group may be associated with a transaction quantity and/or transaction range over the pre-determined period of time. The status filter may automatically filter for merchants based on a transaction quantity then sort into a corresponding group based on the transaction quantity and/or transaction range. A first group may be associated with a first transaction range, a second group with a second transaction range, a third group with a third transaction range, a fourth group with a fourth transaction range, and so forth.

A member status algorithm may include automatically applying one or more status rules. The one or more status rules may function to assign a membership status to one or more merchants based on the result from the status filter. Each group of merchants found by the status filter may be automatically assigned a membership status. Each group may be pre-associated with a status. For example, a first group may be associated with a first status. Once the merchants are sorted into groups, the one or more status rules may automatically apply the membership associated with the group to the merchants within the group. For example, membership statuses may include platinum, gold, silver, and bronze. Based on this example, a platinum status may be assigned to the merchants sorted into the first (e.g., platinum) group, a gold status may be assigned to the merchants sorted into the second (e.g., gold) group, a silver status may be assigned to the merchants sorted into the third (e.g., silver) group, and a bronze status may be assigned to the merchants sorted into the forth (e.g., bronze) group. A member status may be automatically displayed in one or more user interfaces in the transaction system. A member status may be displayed on a dashboard, posting page, marketplace page, transaction, confirmation page after a transaction is completed, user account settings section of the transaction system, a header of the transaction system, the like, or any combination thereof.

Illustrative Embodiments

FIG. 1 illustrates a schematic of an exemplary transaction system 200. The transaction system 200 may have a plurality of servers 202. One server may be an application server 204. One server may be a web server 206. As an alternative, only a web server 206 may be utilized. The servers 202 include one or more processors 208 and one or more memory storage devices 210. The one or more memory storage devices 210 may store one or more databases, computer executable instructions, or both. The transaction system 200 is in communication with and/or includes a plurality of computing devices 212. Computing devices 212 may include one or more personal computers 214, tablets 216, and mobile phones 218. The computing devices 212 may be associated with merchants 220. The computing devices 212 may be physically located at a merchant location, accessible by a user associated with the merchant 220, or both. The merchants 220 may be regulated product merchants, such as pharmacies. The merchants 220 include a first merchant 222 and a second merchant 224. The first merchant 222, user(s) associated with the first merchant 222, or both may be considered a buyer 226. The second merchant 224, user(s) associated with the second merchant 224, or both may be considered a seller 228. The computing devices 212 and the servers 202 may be in communication with and/or form a network 230. The computing devices 212 and servers 202 may be in communication over the Internet 232.

Figure 2:
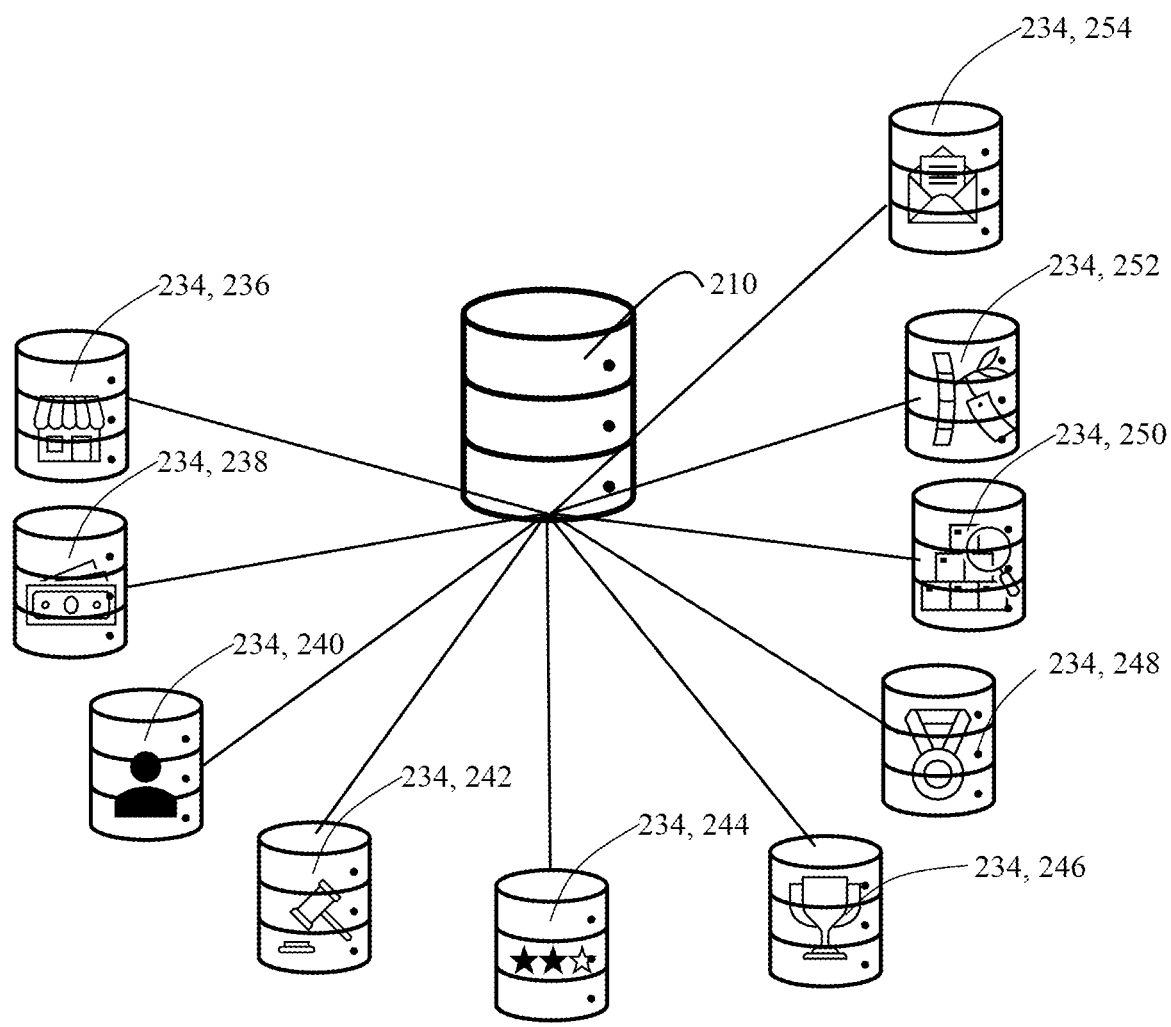
FIG. 2 illustrates a plurality of databases within one or more memory storage devices.

FIG. 2 illustrates one or more memory storage devices 210. The one or more memory storage devices 210 may store one or more databases 234. One or more databases 234 may include one or more merchant account databases 236, banking databases 238, user account databases 240, jurisdiction requirement databases 242, member rating databases 244, rewards databases 246, member status databases 248, inventory databases 250, wishlist databases 252, communications databases 254, and the like. Any combination of a plurality of databases 234 shown as separate databases may be merged as a single database 234.

Figure 3:
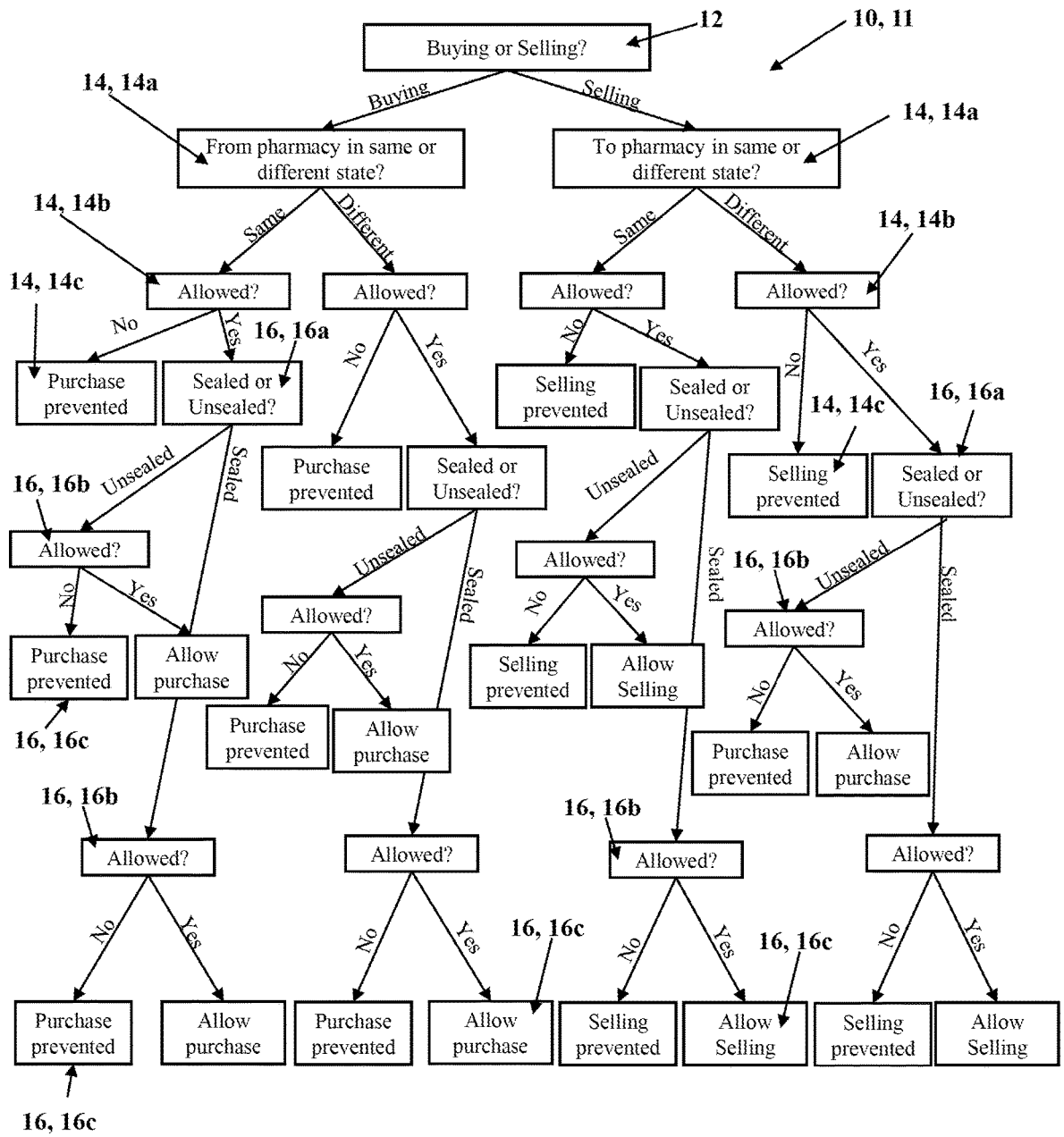
FIG. 3 illustrates a process flow for executing one or more validation heuristics.

FIG. 3 illustrates a process flow for executing one or more validation heuristics 10, such as a marketplace heuristic, applied for the purchase of regulated products, such as pharmaceutical products. The validation heuristic 10 applies a plurality of jurisdiction-based rules 11. The validation heuristic 10 includes a seller buyer determination step 12. During the seller buyer determination step 12, it is determined if the user of the pharmacy account (e.g., first pharmacy or second pharmacy) is acting in a selling capacity to sell pharmaceutical products through the system or if the user is acting in a buying capacity to purchase pharmaceutical products through the system. After the seller buyer determination step 12, the jurisdiction-based rules 11 are applied.

The first jurisdiction rule applied is the participating jurisdiction rule 14. During the same or different jurisdiction rule 14, it is determined if the other pharmacy (e.g., opposite of first pharmacy or second pharmacy) is located in a same or different jurisdiction as the user 14a. After determining the jurisdiction location 14a, it is then determined if the purchase or sale from the first pharmacy is allowed relative to the second pharmacy 14b. If the purchase or sale is not allowed, due to not being compliant with the participating jurisdiction rule 14, then the purchase or sale is prevented 14c. If the purchase or sale is allowed, due to being compliant with the participating jurisdiction rule 14, then the purchase or sale may be allowed, or at least not prevented under the participating jurisdiction rule 14. If the purchase or sale is not prevented, the participating jurisdiction rule 14 moves on to a partial package rule 16.

The second jurisdiction-based rule applied is the partial package rule 16. During the partial package rule 16, it is determined if the first pharmacy is trying to purchase or sell an unsealed (e.g., partially used) package 16*a*. Thus, it is first determined in 16*a* if the package is seal or unsealed. After determining if the package is unsealed 16*a*, it is then determined if the purchase or sale from the first pharmacy is allowed relative to the second pharmacy 16*b*. If the purchase or sale of a sealed or unsealed package from the first pharmacy to the second pharmacy is not allowed, the purchase or sale is prevented in 16*c*. If the purchase or sale of a sealed or unsealed package from the first pharmacy to the second pharmacy is allowed, then the transaction is able to continue under 16*c*.

Figure 4:
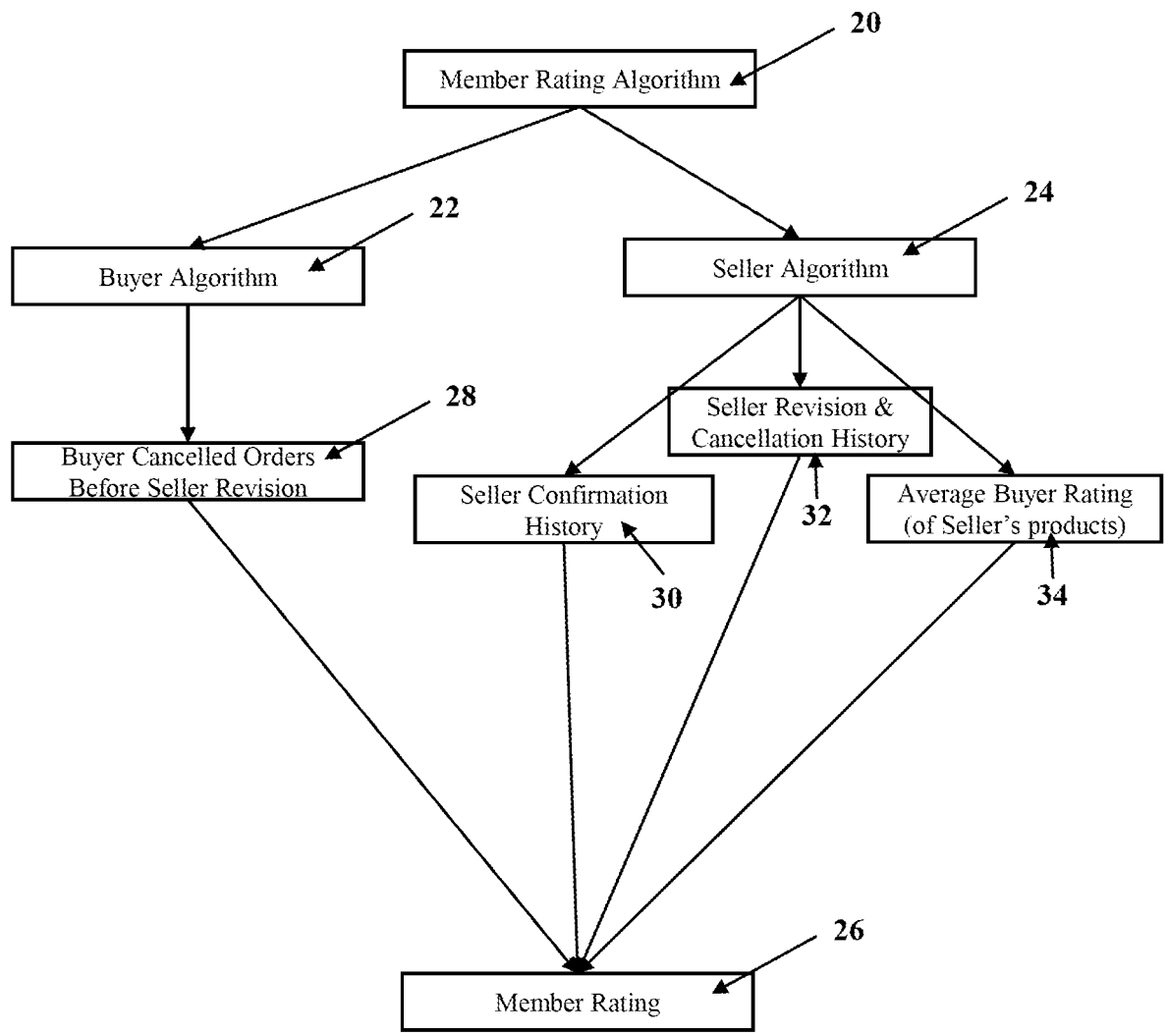
FIG. 4 illustrates a process flow for execution of a member rating algorithm.

FIG. 4 illustrates a process flow for execution of a member rating algorithm 20. The member rating algorithm 20 applies one or more buyer algorithms 22 and one or more seller algorithms 24 to determine a member rating 26. The one or more buyer algorithms 22 include a buyer cancellation sub-algorithm 28. An exemplary buyer cancellation sub-algorithm 28 may determine a percent of orders cancelled by a buyer before revision or cancellation by a seller. Based on the percent of orders cancelled, the percentage may be converted over to a buyer cancellation rating.

The one or more seller algorithms 24 include a seller confirmation sub-algorithm 30, a seller revision sub-algorithm 32, and buyer feedback sub-algorithm 34. A seller confirmation sub-algorithm 30 may determine how quickly a seller confirms an order from a buyer. Based on how quickly a seller confirms an order, a percentage may be determined. The percentage may be converted over to a seller confirmation rating. A seller revision and cancellation sub-algorithm 32 may determine a percent of orders which are revised (revision may include changing or cancelling) by a seller. Based on the percent of orders revised, the percentage may be converted over to a seller revision rating. A buyer feedback sub-algorithm 34 may calculate an average buyer rating. The average buyer rating may be from previous buyers who purchased one or more products from the seller. The average buyer rating may be converted to buyer feedback rating.

After ratings are determined using the one or more buyer algorithms 22 and one or more seller algorithms 24, the one or more ratings are averaged to determine the overall member rating 26.

Figure 5:
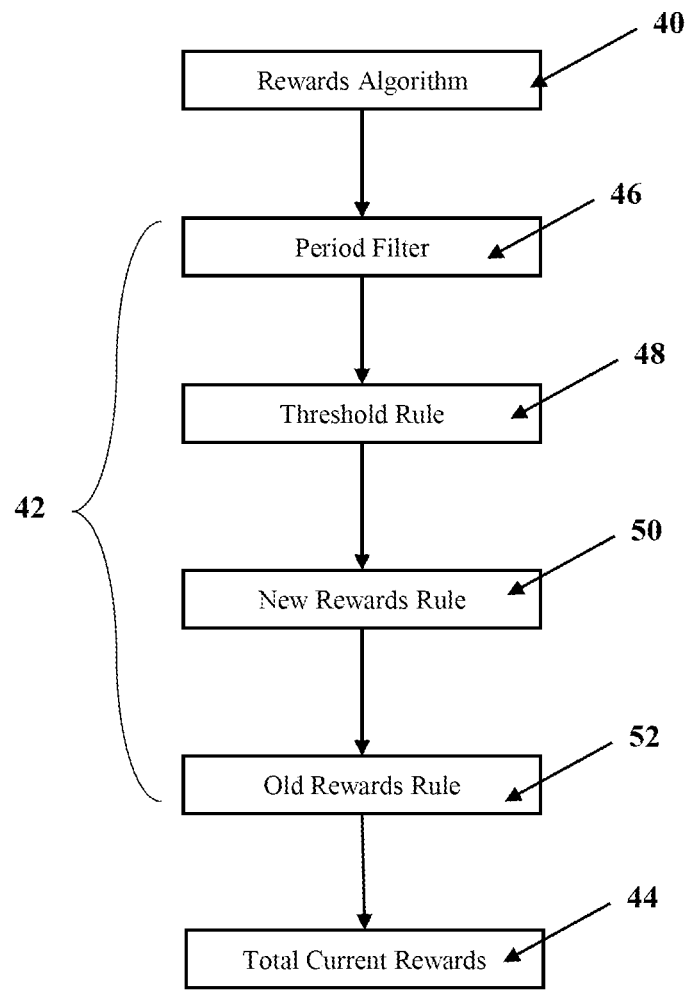
FIG. 5 illustrates a process flow for execution of a rewards algorithm.

FIG. 5 illustrates a process flow for execution of a rewards algorithm 40. The rewards algorithm 40 applies a number of rewards rules and filters 42 to determine a user's available rewards 44. The rewards rules and filters 42 include a period filter 46, threshold rule 48, new rewards rule 50, and old rewards rule 52. The rewards algorithm 40 may first start by applying a period rule 46. The period rule 46 may filter for users which sold products using the system over a pre-determined period of time, such as one month. After the period rule 46, the rewards algorithm 40 may move on to applying a threshold rule 48. The threshold rule 48 may then filter the users for those who also sold at or above a pre-determined sales minimum. After application of the threshold rule 48, the rewards algorithm 40 applies the new rewards rule 50. Under the new rewards rule 50, the new rewards are determined. New rewards are determined based on the sales total during the pre-determined period of time.

After determining the new rewards, the old rewards rule 52 is applied. Under the old rewards rule 52, awards received from previous periods may carry over, expire, or both. Under the old rewards rule 52, rewards awards to a user over a pre-determined period of time may expire. For example, rewards awarded to a user under the new awards rule 50 two or more months prior to the current timeframe may expire. The old rewards rule 52 determines the amount of rewards which also carry over. Once the old rewards rule 52 is applied, then the total available rewards 44 is determined. The available rewards 44 is determined by adding the new rewards from the new rewards rule 50 with the carryover rewards from the old rewards rule 52.

Figure 6:
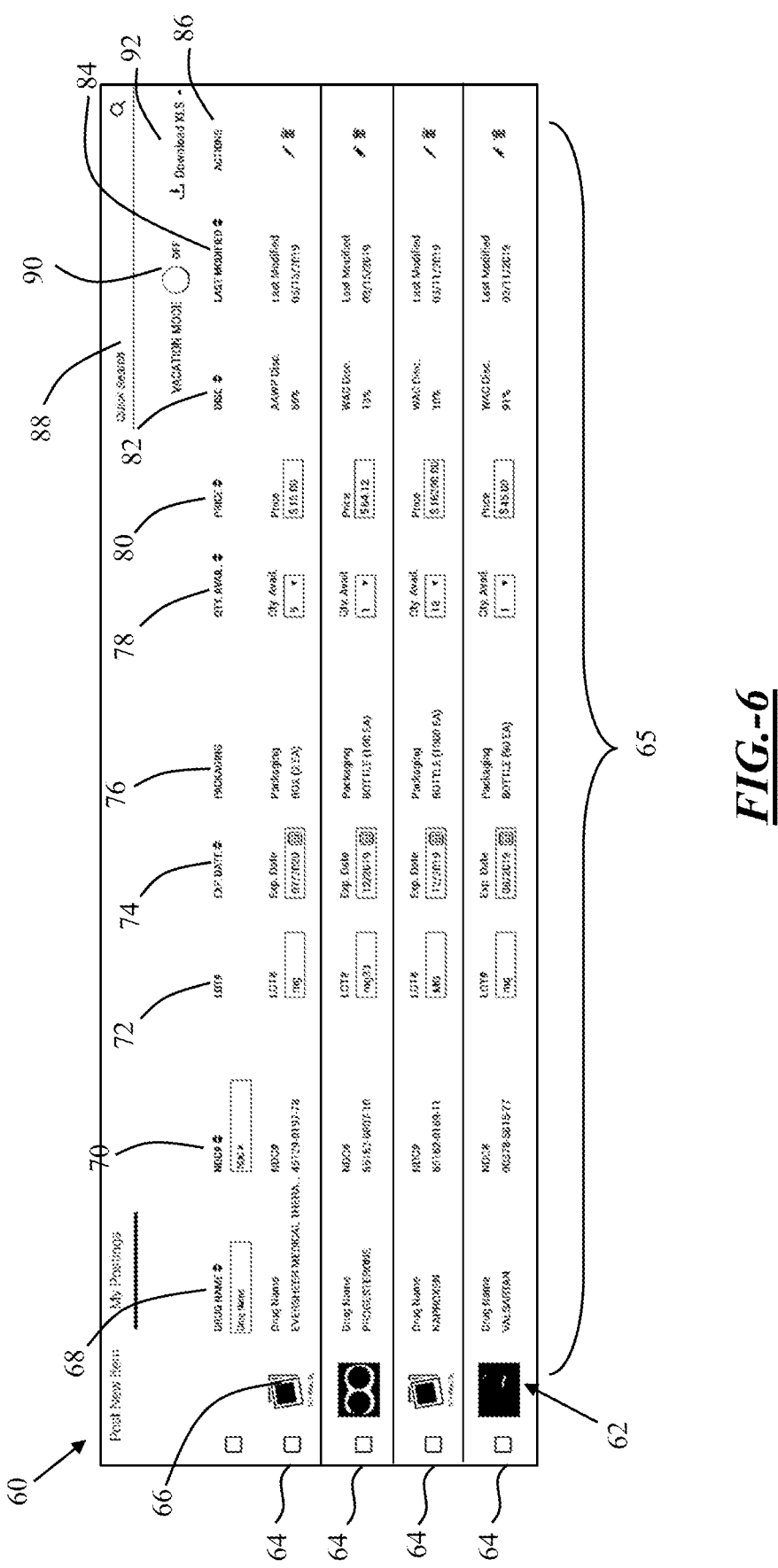
FIG. 6 illustrates a posting page.

FIG. 6 illustrates a posting page 60. The posting page 60 includes a plurality of pharmaceutical products 62 available for sale by a user. The posting page 60 includes all of the pharmaceutical products 62 available for sale by a user such that a user does not need to open other pages. The posting page 60 divides out the pharmaceutical products 62 into individual posting lines 64 by the type of pharmaceutical. Each posting line 64 includes a number of descriptive fields 65. Descriptive fields 65 can include product image 66, a pharmaceutical name 68, a national drug code (NDC) number 70, a lot number 72, an expiration date 74, a packaging type 76, an available quantity 78, a price 80, and a discount type 82, modification date 84, and available actions 86.

The descriptive fields 65 are limited to pre-determined datatypes. The product image 66 can allow for one or more image file types and images. For example, the product image 66 may allow for up to 3 images (e.g., stock image plus 2 actual images). Exemplary image file types can include jpeg, png, gif, tiff, ps, pdf, eps, ai, indd, raw, and the like. The system may convert an image file type from one exemplary image file type to another before storing. For example, the system may convert all image file types to png format before storing. The product image 66 may have a size restriction with respect to the size of the image file, such as 10 MB. The lot number 72 may allow for alphanumeric entries. The alphanumeric entries may be limited to uppercase. If a user types in lowercase within the lot number 72 field, the system may automatically convert to uppercase. The expiration date 74 may be limited to a date entry. The date entry may be possible via a calendar pop-up window, manual entry, or both. The date entry may allow only for dates in the future. The date entry may disable entry of dates within the current month and/or previous months. The packaging type 76 may allow for selection of the type of package based on whether or not the pharmaceutical product 62 is a full or partial package. If the pharmaceutical product 62 is a full package, the system defaults to the known packaging type for that product. If partial, the user is able to select in which type of packaging the pharmaceutical product 62 may be delivered to a purchaser. If partial, the user is able to enter numerical values in addition to selecting a package type, to indicate the size or volume of the package (not the quantity of pharmaceutical product). The available quantity 78 is limited to numerical entries. The price 80 allows for numerical monetary entries. Upon a user selecting the descriptive field 65 for the price 80, the posting page 60 may automatically display a marketplace comparison table (not shown). The marketplace comparison table may be a table that shows average, low, and high prices in the system for the same pharmaceutical product available for sale by other users.

The posting page 60 allows for a user to edit one or more descriptive fields 65 related to one or more pharmaceutical products 62 within the associated posting line 64. For example, a user can edit the lot number 72, the expiration date 74, the available quantity 78, and the price 80. As a user edits one or more descriptive fields 65, the descriptive field 65 may be emphasized. For example, when user edits a descriptive field 65 for a posting line 64, that descriptive field is highlighted or has a background in yellow. After the user edits and exits a descriptive field 65 in a posting line 4464 the field may also be emphasized to show a recent edit. For example, after a user edits and exits a descriptive field 65, that field 65 is highlighted or has a background in green. The posting page 60 also has automatic saving rules applied during editing of one or more descriptive fields 65. As a user is editing a descriptive field 65, the edits are saved at pre-determined time increments without the user initiating the save. For example, edits may be automatically saved every 20 milliseconds.

Upon opening the posting page 60 one or more sorting rules are applied. The one or more sorting rules include a modification rule and a discount rule. The modification rule functions such that upon opening the posting page 60, the plurality of pharmaceutical products 62 and their associated posting line 64 are sorted by the modification date 84 (e.g., ascending or descending chronological order). The discount rule functions such that if there are one or more posting lines 64 where a discount in the discount type 82 is less than a pre-determined value (e.g., Wholesale Acquisition Cost discount is less than 10%), those posting lines 64 are shown first regardless of their modification date. Those posting lines 64 where a discount is less than a pre-determined value may be sorted in ascending order by their respective discount value in the discount type 82. The user is able to sort the individual posting lines 64 by a number of the descriptive fields 65. Once the user initiates a sort by one of the descriptive fields 65, the discount rule with respect to sorting is no longer applied.

The posting page 60 also applies a minimum discount rule. If there is a posting line 64 having a discount under a pre-determined value, the associated discount field 82 in that posting line may be emphasized. For example, the associated discount field 82 may be shown in red font. An alert message (not shown) may be displayed on the posting page 60 if any of the discount fields 82 are beneath a pre-determined value. The alert message may alert the user that the discount field 82 for one or more pharmaceutical products 62 needs to be updated to be at or above the pre-determined value in order to display in the marketplace for purchase. Once a user edits the discount field 82 to be at or above the pre-determined value, an emphasis of the discount field 82 may change. For example, if the discount field 82 was in red font, it may turn into green font.

Upon opening the posting page 60, one or more modification rules are applied. One or more modification rules emphasize text based on when any descriptive field 65 of a posting line 64 was last modified as compared to the current date when the posting page 60 is being viewed. The one or more modification rules may apply a modification timeframe to determine if one or more descriptive fields 65 should be emphasized. For example, a modification timeframe may be 90 days. If one or more descriptive fields 65 have been edited within the modification timeframe, they may not be emphasized. If one or more descriptive fields 65 have not been edited within the modification timeframe, they may be emphasized. For example, if one or more descriptive fields 65 has not been edited within 90 days, the modification date 84 may be emphasized by having the font displayed in red. If one or more descriptive fields 65 have been edited while a user is viewing the posting page 60, one or more descriptive fields 65 may be emphasized. For example, if one or more descriptive fields 65 has been edited on the same day, the modification date 84 may be emphasized by having the font displayed in green.

The posting page 60 also includes a search tool 88. The search tool 68 allows for alphanumeric entries, nonalphanumeric entries, or both. The search tool 88 filters for any posting line 64 which has a descriptive field 65 which matches the input into the search tool 88. The posting page 60 also includes an away mode option 90. The away mode option 90 allows for a user to automatically remove all open postings from the marketplace for a defined and/or undefined period of time. The away mode option 90 may be enabled or disabled by toggling. The posting page 60 also provides for an export function 92. The export function 92 allows for a user to download the plurality of pharmaceutical products 62 and their associated posting lines 64 for offline reference. Upon export, each posting line 64 is converted to a row within a table with each descriptive field 65 associated with a column. Upon export, the descriptive fields 65 are also the header labels of the table.

Figure 7:
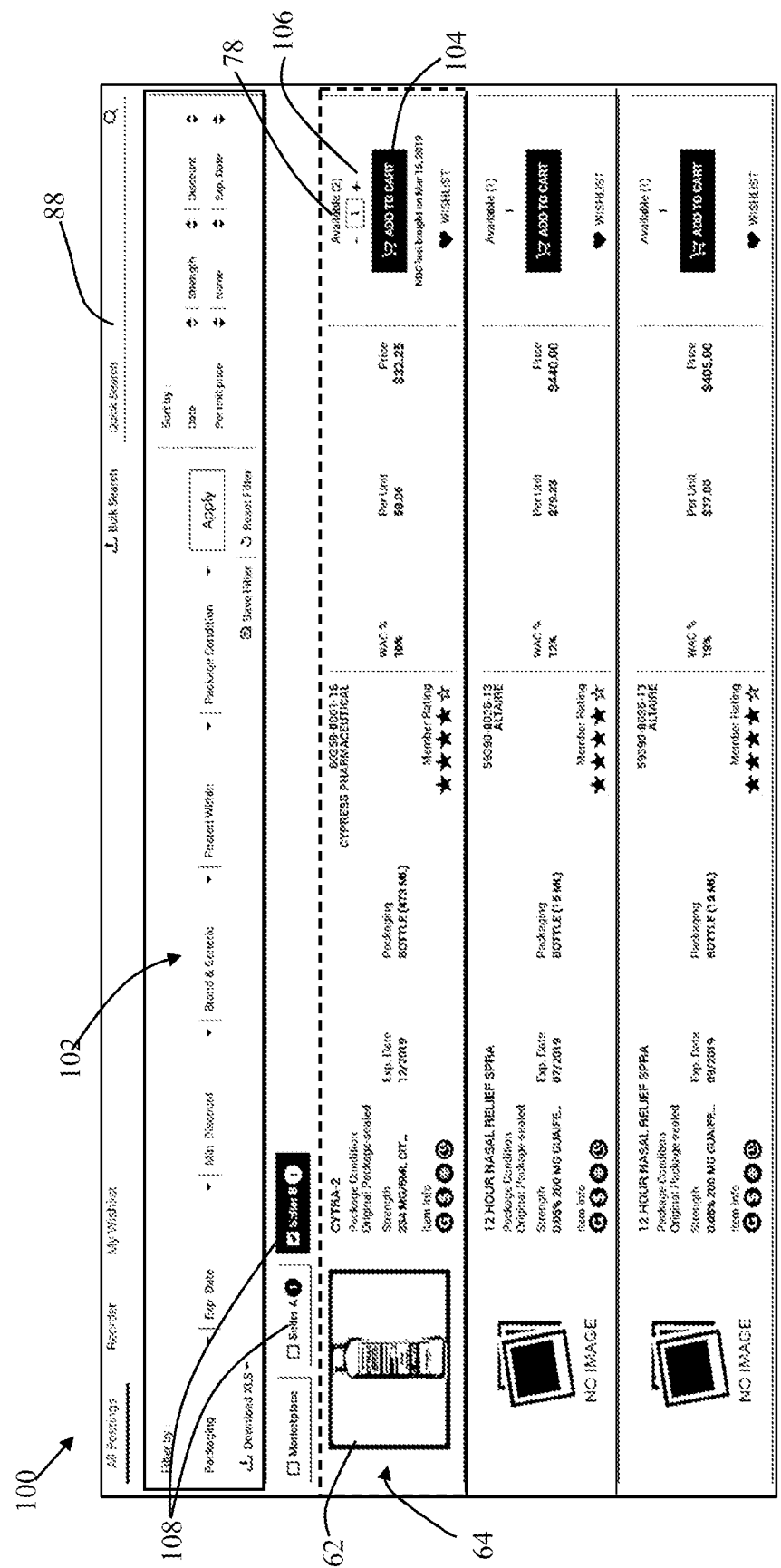
FIG. 7 illustrates a marketplace page.

FIG. 7 illustrates a marketplace page 100 after user has added an item for purchase (e.g., added a pharmaceutical product 62 to their shopping cart). The marketplace page 100 allows for quick searching via a search tool 88. The marketplace page 100 also includes one or more filters 102. The filters 102 allow for filtering the available pharmaceutical products 62 by one or more of the descriptive fields 65. Pharmaceutical products 62 that a user has previously purchased within a pre-determined period of time may be emphasized on the marketplace page 100. The emphasis may occur before or after the use of the search tool 88, applying one or more filters 102, or a combination thereof. Emphasized may mean an entire posting line 64 is highlighted in a color, such as green. A pre-determined period of time may be one month, half a year, a year, or even two or more years. To select a pharmaceutical product 62 for purchase, a user may select an "add to cart" 104 or other purchase button. Once a user selects a pharmaceutical product 62 to purchase, that posting line 64 may be emphasized. Emphasis may include highlighting that posting line 64, such as in yellow or another shade different from other posting lines 64. Once a user selects a product 62 for purchase, the user may modify the purchase quantity 106. A maximum quantity limit is set at the available quantity 78. If additional quantity of the product 62 is not available, the purchase quantity 106 may not be modifiable.

Once a user has selected a product 62 for purchase, the system automatically generates a seller filter 108 which is applied to the marketplace page 100. The seller filter 108 creates a filter which filters all available pharmaceutical products 62 in the system for products 62 being sold by a particular seller. Specifically, the seller is the same seller of the product 62 a user has selected to purchase. The seller filter 108 is displayed as a button or link on the marketplace page 100. If a user has selected multiple products 62 for purchase, multiple seller filters 108 are generated. Each seller filter 108 is associated with a single seller. A user may be able to apply multiple seller filters 108 simultaneously, such that all products 62 available by those multiple sellers are displayed on the marketplace page 80 simultaneously. A user may be restricted as to how many sellers they are able to purchase from in a single transaction. For example, a user may be allowed to select products 62 for purchase from up to five different sellers. The seller filter 108 may be generated for a maximum number of separate sellers. The seller filter 108 may be generated for up to the same maximum that a user is able to purchase from. For example, up to five seller filters 108 may be generated and displayed on the marketplace page 100 which may be the same number of separate sellers a user is able to purchase from in a single transaction. If a user removes an item from a seller from their purchases before completing a transaction, an associated seller filter 108 may be removed from the marketplace page 100.

Figure 8:
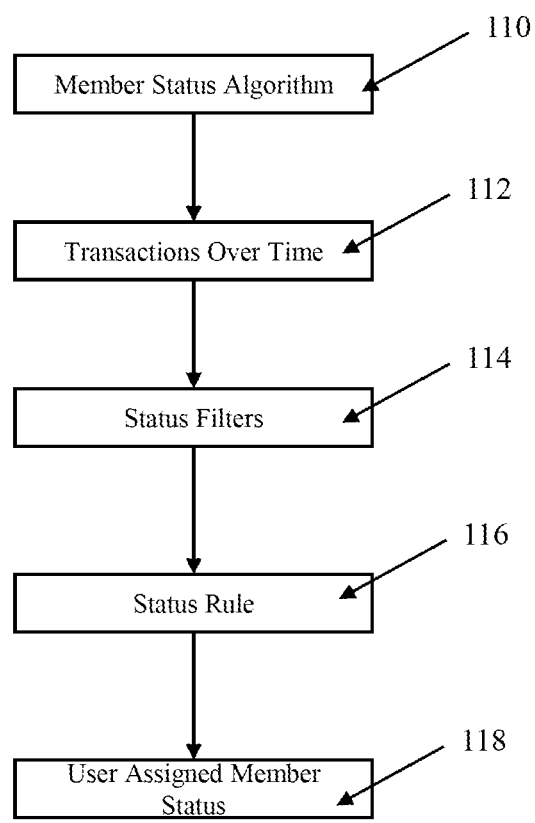
FIG. 8 illustrates a process flow for execution of a member status algorithm.

FIG. 8 illustrates a process flow for execution of a member status algorithm 110. The member status algorithm 110 begins by determining the number of transactions a user had over a pre-determined time period 112. Transactions may include both sales and purchases. A pre-determined time period may be one week, two weeks, one month, three months, or even a year. For example, the pre-determined time period may be three-months. The number of transactions over the pre-determined time period may be referred to as an average of transactions over a portion of the pre-determined time period. For example, the outcome may be the average number of transactions per month over a three-month time period. After determining the number of transactions over the pre-determined time period, one or more status filters 114 are applied. The status filters filter the users based on the transactions which occurred over the pre-determined period of time. For example, there may be four filters: a platinum filter, gold filter, silver filter, and a bronze filter. The platinum filter may filter for users with 20 or more average transactions per month; the gold filter may filter for users with 9 to 19.99 average transactions per month; the silver filter may filter for users with 3 to 8.99 average transactions per month; and the bronze filter may filter for users with less than 3 average transactions per month. After the status filters 114 are applied, a status rule 116 is applied. The status rule 116 assigns a member status based on how the user was filtered with the status filters. Each status may correspond to a filter. For example, the status rule 116 may apply one of four statuses based on the status filter 114. For example, the four statuses may include platinum, gold, silver, and bronze. After the status rule 116 is applied, each user will be assigned a member status 118. A member status may be displayed at multiple points of a user's interaction in the system. For example, member status may be displayed on a confirmation page after a transaction is completed, in a user account settings section of the system, when the user logs in to the system along a header section, etc.

FIG. 9 illustrates an exemplary benefits chart 120. The chart 120 summarizes benefits 124 that may be provided to users based on their member status 122. Exemplary benefits include a transaction limit 126, shipping incentives 128, fee discounts 130, purchase minimums 132, transaction fees 134, early wishlist notifications 136, and pickup fees 138.

Any numerical values recited in the above application include all values from the lower value to the upper value in increments of one unit provided that there is a separation of at least 2 units between any lower value and any higher value. These are only examples of what is specifically intended and all possible combinations of numerical values between the lowest value, and the highest value enumerated are to be considered to be expressly stated in this application in a similar manner. Unless otherwise stated, all ranges include both endpoints and all numbers between the endpoints.

The terms "generally" or "substantially" to describe angular measurements may mean about +/−10° or less, about +/−5° or less, or even about +/−1° or less. The terms "generally" or "substantially" to describe angular measurements may mean about +/−0.01° or greater, about +/−0.1° or greater, or even about +/−0.5° or greater. The terms "generally" or "substantially" to describe linear measurements, percentages, or ratios may mean about +/−10% or less, about +/−5% or less, or even about +/−1% or less. The terms "generally" or "substantially" to describe linear measurements, percentages, or ratios may mean about +/−0.01% or greater, about +/−0.1% or greater, or even about +/−0.5% or greater.

The term "consisting essentially of" to describe a combination shall include the elements, ingredients, components, or steps identified, and such other elements ingredients, components or steps that do not materially affect the basic and novel characteristics of the combination. The use of the terms "comprising" or "including" to describe combinations of elements, ingredients, components, or steps herein also contemplates embodiments that consist essentially of the elements, ingredients, components, or steps.

Plural elements, ingredients, components, or steps can be provided by a single integrated element, ingredient, component, or step. Alternatively, a single integrated element, ingredient, component, or step might be divided into separate plural elements, ingredients, components, or steps. The disclosure of "a" or "one" to describe an element, ingredient, component, or step is not intended to foreclose additional elements, ingredients, components, or steps.

What is claimed is:

1. An electronic transaction system for executing one or more computer-executable instructions for selling and purchasing a plurality of regulated products comprising:
   a) one or more servers comprising one or more processors and one or more memory storage devices;
   b) an application residing on the one or more servers, wherein the application is a computer program which provides for a sale of one or more regulated products from a first merchant to a second merchant, wherein the application includes:
      (i) one or more validation heuristics executable by the one or more processors which automatically confirm compliance of one or more of a plurality of jurisdiction-based rules prior to a completion of the sale of the one or more regulated products from the second merchant to the first merchant;
      (ii) one or more member incentive heuristics executable by the one or more processors which automatically determine one or more incentives available to one or more merchants, wherein the one or more member incentive heuristics include one or more member rating algorithms;
   c) one or more databases hosted by the one or more servers and accessible by the application via the one or more processors, wherein the one or more databases store:
      (i) the plurality of jurisdiction-based rules pertaining to sales and purchases of the plurality of regulated products to and from a plurality of merchants in a plurality of jurisdictions;
      (ii) an inventory of the plurality of regulated products available for sale by the plurality of merchants and available for purchase by the plurality of merchants and which includes the one or more regulated products;
      (iii) one or more member incentives automatically determined by the one or more member incentive heuristics;
      (iv) a plurality of merchant accounts associated with the plurality of merchants;
   d) one or more computing devices with one or more user interfaces in communication with the one or more servers via one or more networks;

wherein the one or more member rating algorithms automatically determine a member rating for the one or more merchants based on interactions with other merchants in the electronic transaction system;

wherein the application is configured to display one or more graphical user interfaces on the one or more user interfaces of the one or more computing devices;

wherein the one or more graphical user interfaces include one or more marketplace pages;

wherein the one or more validation heuristics are configured to be automatically executed such that the one or more marketplace pages only display one or more products of the plurality of regulated products from the inventory which adhere to the plurality of jurisdiction-based rules such that any merchant of the plurality of merchants acting in a buying capacity can only view the one or more products which they are able to purchase while adhering to the plurality of jurisdiction-based rules;

wherein each individual regulated product displayed on the one or more marketplace pages is displayed in a posting line;

wherein the posting line includes a plurality of data related to the individual regulated product, including:
(i) a product image,
(ii) a product name,
(iii) an expiration date,
(iv) the member rating of each merchant selling the individual regulated product;

wherein the one or more marketplace pages are configured to retain anonymity of each of the one or more merchants associated with the one or more products displayed on the one or more marketplace pages;

wherein the one or more validation heuristics include one or more merchant validation heuristics which are automatically executed for each merchant of the plurality of merchants upon the merchant registering and creating a merchant account within the electronic transaction system, wherein the electronic transaction system is configured to communicate directly with one or more external licensing databases, wherein the one or more external licensing databases have licensing and/or permitting information pertaining to the plurality of merchants and the plurality of jurisdictions stored therein;

wherein the one or more merchant validation heuristics automatically access and retrieve from the one or more external licensing databases the licensing and/or permitting information pertaining to the merchant and their respective jurisdiction upon registering with the electronic transaction system and then store the licensing and/or permitting information in the one or more databases, and wherein the one or more merchant heuristics related to retrieving the licensing and/or permitting information from the one or more external licensing databases is executed by the one or more processors only one time for each of the plurality of merchant accounts associated with the plurality of merchants at the time each merchant account is created.

2. The electronic transaction system according to claim 1, wherein the one or more regulated products are one or more pharmaceutical products, the first merchant is a first pharmacy, and the second merchant is a second pharmacy.

3. The electronic transaction system according to claim 1, wherein the plurality of jurisdictions includes a plurality of states; and
wherein the plurality of jurisdiction-based rules include one or more participating jurisdiction rules, partial packaging rules, or both.

4. The electronic transaction system according to claim 3, the one or more validation heuristics include a marketplace validation heuristic which is configured to apply one or more of the plurality of jurisdiction-based rules to determine:
i) a first jurisdiction associated with the first merchant and a second jurisdiction associated with the second merchant; and
ii) the sale of the one or more regulated products from the second merchant to the first merchant is permissible based on the one or more participating jurisdiction rules and a location of the first jurisdiction and the second jurisdiction; and
wherein the electronic transaction system is configured to automatically prevent the sale of the one or more regulated products which is not permissible.

5. The electronic transaction system according to claim 4, wherein the marketplace validation heuristic is configured to be automatically executed by the one or more processors before displaying the one or more marketplace pages to a user associated with the second merchant.

6. The electronic transaction system according to claim 5, wherein the first jurisdiction is different than the second jurisdiction.

7. The electronic transaction system according to claim 1, wherein the one or more validation heuristics include a marketplace validation heuristic which is configured to apply one or more of the plurality of jurisdiction-based rules to determine:
i) if the one or more regulated products include one or more partial packages;
ii) a first jurisdiction associated with the first merchant and a second jurisdiction associated with the second merchant;
iii) if a sale of the one or more partial packages from the second merchant to the first merchant is permissible based on one or more partial packaging rules and a location of the first jurisdiction and the second jurisdiction; and
wherein if the sale of the one or more partial packages is not permissible, the marketplace validation heuristic automatically prevents the sale from being completed.

8. The electronic transaction system according to claim 1, wherein the one or more marketplace pages are configured to retain anonymity of the first merchant and the second merchant from one another.

9. The electronic transaction system according to claim 1, wherein the one or more member incentive heuristics include: one or more rewards algorithms, one or more member status algorithms, or a combination thereof.

10. The electronic transaction system according to claim 9, wherein the one or more member incentive heuristics include the one or more rewards algorithms; and
wherein the one or more rewards algorithms automatically determine a discount usable by the one or more merchants to purchase the one or more regulated products based on their transaction history within the electronic transaction system.

11. The electronic transaction system according to claim 9, wherein the one or more member incentive heuristics include the one or more member status algorithms; and
wherein the one or more member status algorithms automatically determine one or more benefits available to the one or more merchants within the electronic transaction system based on their transaction history within the electronic transaction system.

12. The electronic transaction system according to claim 1, wherein the one or more computing devices and the one or more user interfaces include:
a) a first user interface of a first computing device, wherein the first user interface is accessible by a first user associated with the first merchant; and
b) a second user interface of a second computing device, wherein the second user interface is accessible by a second user associated with the second merchant.

13. A method of executing the one or more computer-executable instructions for selling and purchasing the one or more regulated products via the electronic transaction system according to claim 1, wherein the method comprises:
a) a user, associated with the first merchant, registering for a first merchant account within the electronic transaction system;
b) automatically executing the one or more merchant validation heuristics by the one or more or more processors of the electronic transaction system upon the registering of the first merchant account;
wherein the electronic transaction system is in communication with the one or more external licensing databases, wherein the one or more external licensing databases have the licensing and/or permitting information pertaining to the plurality of merchants and the plurality of jurisdictions stored therein;
wherein the one or more merchant validation heuristics automatically access and retrieve from the one or more external licensing databases the licensing and/or permitting information pertaining to the first merchant and their respective jurisdiction upon the registering of the merchant account and then store the licensing and/or permitting, information in the one or more databases of the electronic transaction system; and
wherein the one or more merchant heuristics related to retrieving the licensing and/or permitting information from the one or more external licensing databases is executed by the one or more processors only one time for the first merchant at the time the first merchant account is created;
c) the user, associated with the first merchant and acting in a capacity of a buyer, opening a marketplace page of the application via a first user interface;
d) automatically executing by the one or more processors at least one of the one or more validation heuristics to identify the plurality of regulated products available for sale by a plurality of second merchants acting in a capacity of a seller and which comply with the plurality of jurisdiction-based rules for both the first merchant and the plurality of second merchants;
e) automatically executing by the one or more processors at least one of the one or more member incentive heuristics, including the one or more member rating algorithms to determine the member rating for each merchant of the plurality of second merchants;
f) automatically displaying the plurality of regulated products identified by the one or more validation heuristics on the marketplace page such that only the plurality of regulated products which comply with the plurality of jurisdiction-based rules are displayed on the marketplace page, wherein each individual regulated product is displayed on the marketplace page in the posting line and the posting line displays the member rating of the second merchant selling the individual regulated product, and wherein an identity of the plurality of second merchants remains anonymous on the marketplace page;
g) the user selecting the one or more regulated products from the marketplace page from the second merchant for purchase; and
h) automatically executing automated payment from the first merchant to the second merchant to complete the purchase of the one or more regulated products.

14. The method of claim 13, wherein the one or more regulated products are one or more pharmaceutical products, the first merchant is a first pharmacy, and the second merchant is a second pharmacy.

15. The method of claim 13, wherein the one or more validation heuristics include a marketplace validation heuristic which automatically applies one or more of the plurality of jurisdiction-based rules and includes:
a) determining a first jurisdiction associated with the first merchant and a second jurisdiction associated with the second merchant;
b) determining if the sale of the one or more regulated products from the second merchant to the first merchant is permissible based on one or more participating jurisdiction rules and a location of the first jurisdiction and the second jurisdiction; and
c) automatically prevents a sale of non-compliant regulated products which do not comply with the one or more participating jurisdiction rules by automatically not displaying the non-compliant regulated products on the marketplace page.

16. The method of claim 13, wherein the one or more validation heuristics include a marketplace validation heuristic which automatically applies one or more of the plurality of jurisdiction-based rules and includes:
a) determining if the one or more regulated products include one or more partial packages;
b) determining a first jurisdiction associated with the first merchant and a second jurisdiction associated with the second merchant;
c) determining if a sale of the one or more partial packages from the second merchant to the first merchant is permissible based on one or more partial packaging rules and a location of the first jurisdiction and the second jurisdiction; and
d) automatically preventing the sale of the one or more partial packages from the second merchant to the first merchant if the sale does not comply with the one or more partial packaging rules by automatically not displaying the one or more partial packages of the one or more regulated products on the marketplace page.

17. The method of claim 13, wherein the user is unable to determine an identity of the plurality of second merchants from the marketplace page as the identity of the plurality of merchants remain anonymous until a transaction within the electronic transaction system is completed.

18. The method of claim 13, wherein the method includes automatically executing the one or more member incentive heuristics to determine the one or more member incentives; and
automatically applying the one or more member incentives prior to the automated payment.

19. The method of claim 13, wherein the one or more member rating algorithms determine the member rating based on behavior of the plurality of merchants when acting in the buying capacity and a selling capacity.

20. The method of claim 19, wherein the one or more member rating algorithms determine the member rating based on the behavior in the electronic transaction system including cancelled orders, orders with payment rejections, confirmation history, revision history, cancellation history, delivery timing, or a combination thereof.

* * * * *